United States Patent
Fobel et al.

(10) Patent No.: US 9,594,056 B2
(45) Date of Patent: Mar. 14, 2017

(54) PRINTED DIGITAL MICROFLUIDIC DEVICES METHODS OF USE AND MANUFACTURE THEREOF

(71) Applicant: THE GOVERNING COUNCIL OF THE UNIVERSITY OF TORONTO, Toronto (CA)

(72) Inventors: Ryan Fobel, Toronto (CA); Andrea Kirby, Toronto (CA); Aaron Wheeler, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 115 days.

(21) Appl. No.: 14/192,737

(22) Filed: Feb. 27, 2014

(65) Prior Publication Data

US 2015/0107998 A1 Apr. 23, 2015

Related U.S. Application Data

(60) Provisional application No. 61/894,827, filed on Oct. 23, 2013.

(51) Int. Cl.
*G01N 27/447* (2006.01)
*B81C 1/00* (2006.01)

(52) U.S. Cl.
CPC ... *G01N 27/44791* (2013.01); *B81C 1/00166* (2013.01); *B81B 2201/058* (2013.01); *B81C 2201/0184* (2013.01); *B81C 2201/0185* (2013.01)

(58) Field of Classification Search
CPC .............. G01N 27/447; B81C 1/00166; B81C 2201/0184–2201/185; B81B 2201/058
See application file for complete search history.

(56) References Cited

U.S. PATENT DOCUMENTS

| 8,053,239 | B2 | 11/2011 | Wheeler et al. |
| 8,187,864 | B2 | 5/2012 | Wheeler et al. |
| 8,394,249 | B2 | 3/2013 | Pollack et al. |
| 2008/0169197 | A1* | 7/2008 | McRuer et al. ............ 204/600 |
| 2010/0081578 | A1 | 4/2010 | Wheeler et al. |
| 2010/0213074 | A1 | 8/2010 | Mousa et al. |
| 2011/0024793 | A1 | 2/2011 | Jeon |

(Continued)

OTHER PUBLICATIONS

Bollstrom, Organic Electronics 10 (2009) 1020-1023.*

(Continued)

*Primary Examiner* — Jennifer Dieterle
(74) *Attorney, Agent, or Firm* — Shay Glenn LLP

(57) ABSTRACT

Embodiments of the present disclosure digital microfluidic arrays that may be fabricated by a printing method, whereby digital microfluidic electrodes arrays are printed, via a printing method such as inkjet printing, onto a suitable substrate. In some embodiments, a substrate and/or ink is prepared or modified to support the printing of electrode arrays, such as via changes to the surface energy. In some embodiments, porous and/or fibrous substrates are prepared by the addition of a barrier layer, or, for example, by the addition or infiltration of a suitable material to render the surface capable of supporting printed electrodes. Various example embodiments involving hybrid devices formed by the printing of digital microfluidic arrays onto a substrate having a hydrophilic layer are disclosed.

27 Claims, 18 Drawing Sheets

(56) References Cited

U.S. PATENT DOCUMENTS

| | | | |
|---|---|---|---|
| 2011/0247934 A1 | 10/2011 | Wang et al. | |
| 2011/0293851 A1* | 12/2011 | Bollstrom et al. | 427/536 |
| 2012/0044299 A1* | 2/2012 | Winger | 347/54 |
| 2012/0083046 A1 | 4/2012 | Watson et al. | |
| 2012/0085645 A1 | 4/2012 | Mousa et al. | |
| 2013/0062205 A1 | 3/2013 | Hadwen et al. | |
| 2013/0164856 A1 | 6/2013 | Jebrail et al. | |
| 2013/0171546 A1 | 7/2013 | White et al. | |
| 2013/0178374 A1 | 7/2013 | Eckhardt et al. | |
| 2013/0215492 A1 | 8/2013 | Steckl et al. | |
| 2013/0284956 A1* | 10/2013 | Kwon | 251/65 |

OTHER PUBLICATIONS

A. W. Martinez, S. T. Phillips, M. J. Butte, G. M. Whitesides, Angew. Chem. Int. Ed. 2007, 46, 1318-1320.
W. Zhao, A. van den Berg, Lab. Chip 2008, 8, 1988-1991.
X. Li, D. R. Ballerini, W. Shen, Biomicrofluidics 2012, 6, 011301.
G. E. Fridley, H. Q. Le, E. Fu, P. Yager, Lab. Chip 2012, 12, 4321-4327.
A. W. Martinez, S. T. Phillips, E. Carrilho, S. W. Thomas, H. Sindi, G. M. Whitesides, Anal. Chem. 2008, 80, 3699-3707.
C.-M. Cheng, A. W. Martinez, J. Gong, C. R. Mace, S. T. Phillips, E. Carrilho, K. A. Mirica, G. M. Whitesides, Angew. Chem. Int. Ed. 2010, 49, 4771-4774.
A. W. Martinez, S. T. Phillips, G. M. Whitesides, Proc. Natl. Acad. Sci. 2008, 105, 19606-19611.
H. Liu, R. M. Crooks, J. Am. Chem. Soc. 2011, 133, 17564-17566.
E. Fu, B. Lutz, P. Kauffman, P. Yager, Lab. Chip 2010, 10, 918-920.
X. Li, J. Tian, T. Nguyen, W. Shen, Anal. Chem. 2008, 80, 9131-9134.
A. V. Govindarajan, S. Ramachandran, G. D. Vigil, P. Yager, K. F. Böhringer, Lab. Chip 2011, 12, 174-181.
J. Tian, X. Li, W. Shen, Lab. Chip 2011, 11, 2869-2875.
J. Yan, L. Ge, X. Song, M. Yan, S. Ge, J. Yu, Chem.—Eur. J. 2012, 18, 4938-4945.
S. Wang, L. Ge, X. Song, J. Yu, S. Ge, J. Huang, F. Zeng, Biosens. Bioelectron. 2012, 31, 212-218.
S. Wang, L. Ge, X. Song, M. Yan, S. Ge, J. Yu, F. Zeng, Analyst 2012, 137, 3821-3827.
J. Yan, M. Yan, L. Ge, J. Yu, S. Ge, J. Huang, Chem. Commun. 2013, 49, 1383-1385.
K. Choi, A. H. C. Ng, R. Fobel, A. R. Wheeler, Annu. Rev. Anal. Chem. 2012, 5, 413-440.
P. Y. Paik, V. K. Pamula, M. G. Pollack, K. Chakrabarty, in Proc Intl Conf MicroTAS, 2005, pp. 566-568.
J. Gong, C. J. Kim, in Proc. IEEE MEMS, Miami, Florida, 2005, pp. 726-729.
M. Abdelgawad, A. R. Wheeler, Adv. Mater. 2007, 19, 133-137.
M. Abdelgawad, A. Wheeler, Microfluid. Nanofluidics 2008, 4, 349-355.
R. Fobel, C. Fobel, A. R. Wheeler, Appl. Phys. Lett. 2013, 102, 193513.
J. Banatvala, D. Brown, The Lancet 2004, 363, 1127-1137.
K. Choi, A. H. A H. C. Ng, R. Fobel, D. A. Chang-Yen, L. E. Yarnell, E. L. Pearson, C. M. Oleksak, A. T. Fischer, R. P. Luoma, J. M. Robinson, J. Audet, A. R. Wheeler, Anal. Chem. 2013, DOI 10.1021/ac401847x.
L. P. Skendzel, Am. J. Clin. Pathol. 1996, 106, 170-174.
A. H. C. Ng, K. Choi, R. P. Luoma, J. M. Robinson, A. R. Wheeler, Anal. Chem. 2012, 84, 8805-8812.
R. Bollström, A. Määttänen, D. Tobjörk, P. Ihalainen, N. Kaihovirta, R. Österbacka, J. Peltonen, M. Toivakka, Org. Electron. 2009, 10, 1020-1023.
D. Tobjörk, H. Aamio, P. Pulkkinen, R. Bollström, A. Määttänen, P. Ihalainen, T. Mäkelä, J. Peltonen, M. Toivakka, H. Tenhu, R. Österbacka, Thin Solid Films 2012, 520, 2949-2955.
P. Ihalainen et al., Biosensors 2013, 3, 1-17.
A. J. Steckl, Proc. of SPIE vol. 7956 795607 (2011).
J. Peltonen, TAPPI Nanotechnology, Espoo, Finland (2010).
A. Denneulin et al., J. Nanopart. Res. 2011, 13:3815-3823.
A. Abdelgawad, Digital Microfluidics for Integration of Lab-on-a-Chip Devices, Ph. D. Thesis, University of Toronto, 2009.
M. Abdelgawad and A. Wheeler, Adv. Mater. 2007, 19, 133-137.
D. Liana et al., Sensors 2012, 12, 11505-11526.
International Search Report for corresponding PCT application No. PCT/CA2014/050142, mailed Jul. 21, 2014.

* cited by examiner

PRINTED DIGITAL MICROFLUIDIC DEVICES METHODS OF USE AND MANUFACTURE THEREOF

CROSS-REFERENCE TO RELATED APPLICATION

This application claims priority to U.S. Provisional Application No. 61/894,827, titled "PRINTED DIGITAL MICROFLUIDIC DEVICES METHODS OF USE AND MANUFACTURE THEREOF" and filed on Oct. 23, 2013, the entire contents of which is incorporated herein by reference.

BACKGROUND

The present disclosure relates to digital microfluidic devices and methods.

Paper microfluidics, employing microfluidic channels formed within paper substrates, has recently emerged as simple and low-cost paradigm for fluid manipulation and diagnostic testing [1-3]. When compared to traditional "lab-on-a-chip" technologies, paper microfluidics has several distinct advantages that make it especially suitable for point-of-care testing in low-resource settings. The most obvious benefits are the low cost of paper and the highly developed infrastructure of the printing industry, making production of paper-based devices both economical and scalable [3]. Other important benefits include the ease of disposal, stability of dried reagents [4] and the reduced dependence on expensive external instrumentation[5,6].

While the paper microfluidics concept has transformative potential, this class of devices is not without drawbacks. Many assays have limited sensitivity in the paper format because of reduced sample volumes and limitations of colorimetric readouts [6]. These devices, being inherently channel-based, also exhibit large dead volumes as the entire channel must be filled to drive capillary flow. Perhaps the most significant challenge for paper-based microfluidic devices is a product of their passive nature itself, making it difficult to perform complex multiplexing and multi-step assays (e.g., sandwich ELISA).

There has been progress in expanding device complexity through the development of three-dimensional channel networks [7,8] and adapting channel length, width and matrix properties can provide control of reagent sequencing and time of arrival at specific points on the device [9]. Active "valve" analogues have also been demonstrated using cut-out fluidic switches [10] and manual folding [11] however, these techniques require operator intervention which can introduce additional complications.

Some groups have implemented complicated, multi-step assays including sandwich ELISA using paper "well plates" and manual pipetting [6,12-16]. These assays are analogous to those performed in standard 96-well polystyrene plates, but the "plates" are pieces of paper patterned with hydrophobic/hydrophilic zones. The drawback to this class of devices is that they are not truly "microfluidics"—unlike the methods described above, each reagent must be pipetted into a given well to implement an assay, similar to conventional multiwell plate techniques.

SUMMARY

Embodiments of the present disclosure digital microfluidic arrays that may be fabricated by a printing method, whereby digital microfluidic electrodes arrays are printed, via a printing method such as inkjet printing, onto a suitable substrate. In some embodiments, a substrate and/or ink is prepared or modified to support the printing of electrode arrays, such as via changes to the surface energy. In some embodiments, porous and/or fibrous substrates are prepared by the addition of a barrier layer, or, for example, by the addition or infiltration of a suitable material to render the surface capable of supporting printed electrodes.

Accordingly, in one embodiment, there is provided a digital microfluidic device comprising:
  a porous substrate having a surface adapted to support electrodes thereon;
  an array of digital microfluidic electrodes printed on said porous substrate; and
  a dielectric layer coating said array of digital microfluidic electrodes, wherein a surface of said dielectric layer is hydrophobic;
  wherein an inter-electrode trench depth, and inter-electrode trench width, and the surface roughness of said array of digital microfluidic electrodes are suitable for transporting droplets among electrodes under electrical actuation.

In another embodiment, there is provided a method of fabricating a digital microfluidic device, the method comprising:
  providing a substrate;
  printing, with a conductive ink, an array of digital microfluidic electrodes onto said substrate; and
  coating said array of digital microfluidic electrodes with a dielectric layer having a hydrophobic surface;
  wherein said substrate has a surface roughness such that a surface roughness of said digital microfluidic device, after coating said array of digital microfluidic electrodes, is less than approximately 1 micron; and
  wherein said conductive ink and surface properties of said substrate are selected such that a surface energy of droplets of conductive ink printed on said substrate are suitable for forming said electrodes.

In another embodiment, there is provided a digital microfluidic device comprising:
  a porous substrate having a surface adapted to support electrodes thereon;
  an array of digital microfluidic electrodes formed on said porous substrate; and
  a dielectric layer coating said array of digital microfluidic electrodes, wherein a surface of said dielectric layer is hydrophobic;
  wherein an inter-electrode trench depth, and inter-electrode trench width, and the surface roughness of said array of digital microfluidic electrodes are suitable for transporting droplets among electrodes under electrical actuation.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1A:
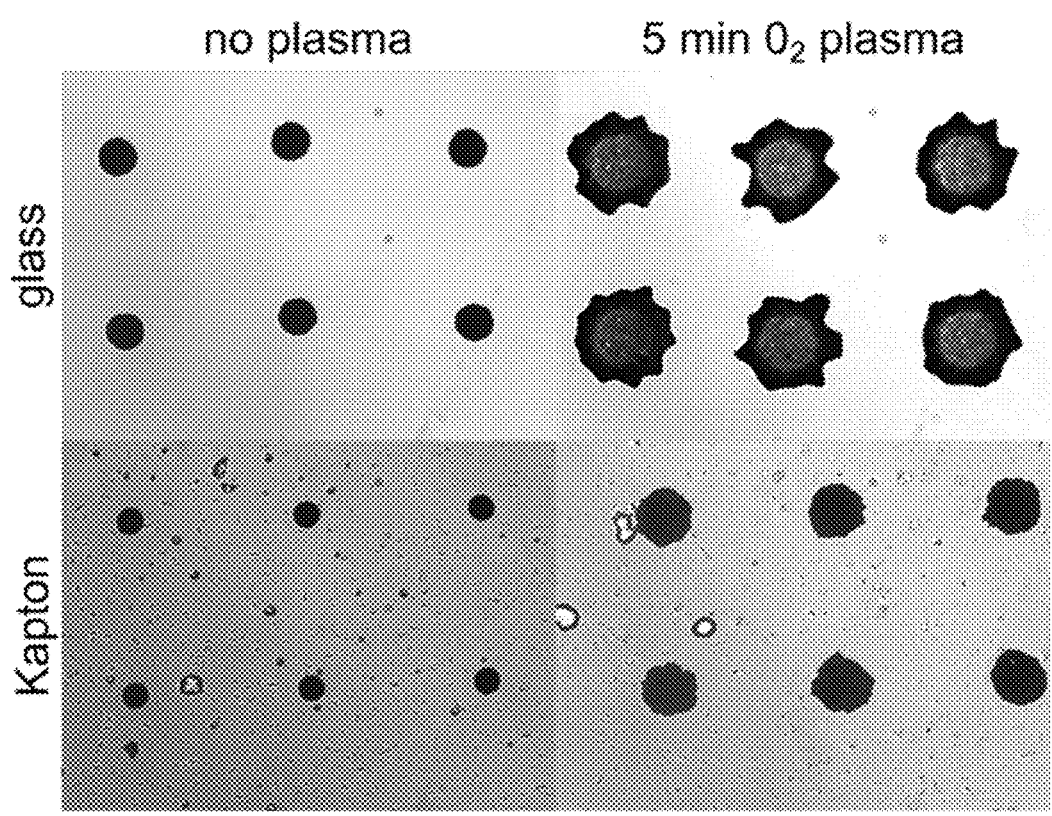
FIG. 1A is image of a test pattern (dots spaced on a 254 micron grid) printed on glass and kapton, both with and without 5 min of oxygen-plasma treatment, show the effect of surface energy on ink droplet formation.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

Digital microfluidics (DMF) is a technology platform for manipulating nano-to-microliter-sized liquid drops on an array of electrodes using electric fields. Electrostatic forces can be used to merge, mix, split, and dispense drops from reservoirs, all without pumps or moving parts.

While DMF has been applied to a wide range of applications [17], a significant challenge has been the lack of a scalable and economical method of device fabrication—most academic labs use photolithography in cleanroom facilities to form patterns of electrodes on glass and silicon. One scalable technique is the use of printed circuit board (PCB) fabrication to form DMF devices [18-20]. Unfortunately, such devices suffer from performance problems associated with the thick nature of the electrodes, which hinder reliable and efficient droplet actuation and transport.

Embodiments of the present disclosure provide digital microfluidic arrays that may be fabricated by a printing method, whereby digital microfluidic electrodes arrays are printed, via a printing method such as inkjet printing, onto a substrate. In some embodiments, the substrates and/or inks are prepared or modified to support the printing of electrode arrays, such as via changes to the surface energy. In some embodiments, porous and/or fibrous substrates are prepared by the addition of a barrier layer, or, for example, by the addition or infiltration of a suitable material to render the surface capable of supporting printed electrodes.

As described below, the printed digital microfluidic arrays formed according to the methods disclosed herein have been found to overcome many of the performance limitations associated with PCB-based digital microfluidic devices. Furthermore, according to some embodiments, digital microfluidic devices may be efficiently and inexpensively fabricated on low-cost substrates, such as polymer- and paper-based substrates using simple and scalable printing methods such as inkjet printing. Such methods may offer superior performance and be better suited for rapid prototyping and/or production.

In one example embodiment, a digital microfluidic device is fabricated by the direct printing an array of digital microfluidic electrodes onto a substrate. Unlike conventional methods for forming digital microfluidic arrays and devices, the direct printing methods disclosed herein provide a rapid and cost effective method for DMF fabrication that may be readily scaled. According to one example implementation, an array of digital microfluidic electrodes may be formed via inkjet printing. The fabrication techniques described herein may be scaled to larger scale processes, such as a roll-to-roll processes [27,28].

A wide variety of conductive inks or liquids may be employed for the formation of digital microfluidic electrodes via a printing process such as inkjet printing. In one non-limiting example, silver nanoparticle-based inks are employed for the formation of digital microfluidic arrays onto a surface. Commercially available inks that may be used include SunTronic U5603 (Sun Chemical), Cabot Conductive Ink CCI-300, and Xerox 32% Nanosilver Ink.

In some embodiments, moderately conductive inks may be employed. For example, traces formed via the deposition of moderately conductive inks may have resistances greater than >20 kOhms, for example, up to approximately 200 kOhms, or higher, given suitable operating conditions.

Organic polymer inks may alternatively be employed for the formation of digital microfluidic electrodes on a substrate. For example, inks such as PEDOT:PSS, inks containing other metals (e.g., copper), may be employed, either as a suspensions of nanoparticles, or in solution (e.g., silver nitrate). Other types of inks, such as those containing carbon nanotubes, etc., may also be employed.

The inkjet printing method may be controlled to prevent the clogging of printing nozzles. For example, the present inventors found that during experimental development of an inkjet printing method, problems were encountered involving the clogging of nozzles during inkjet printing. Such problems can occur because the inks contain particles in suspension (which is true of most conductive inks). It was found that filtering the ink prior to use improved the performance of the printing and reduced or avoiding clogging. In one example, 0.45 μm nylon filter was employed to filter the ink prior to loading it into the cartridge. Furthermore, the ink bottle and loaded cartridges were maintained at a temperature of 4 degrees Celsius when not in use.

It was also found that when employing methods involving inkjet printing, the print head cleaning pad, supplied by the printer manufacturer (Dimatix) was not well suited to the particle-based conductive inks that were used to produce the digital microfluidic devices described herein. The cleaning pad provided was an adsorbent cellulose pad, over which the printer can be programmed to periodically purge ink from the nozzles and/or to blot excess ink from the print head by bringing it into temporary contact with the cleaning pad. With these conductive inks, this procedure is ineffective because the cleaning pad quickly becomes saturated. It was found that wrapping the cellulose cleaning pad with a lint-free paper towel (e.g., Kimwipes), and gently wiping the print head manually with a paper towel soaked in a 50/50 mixture of ethanol/ethylene glycol dramatically reduced the occurrence of clogged nozzles.

It is further noted that the jetting waveform was tuned (timing and amplitude) to achieve stable jetting behavior. Initially, the waveform and parameters supplied by the ink manufacturer was employed. Adjustments were made to improve drop velocity, shape, trajectory, etc. while observing a real-time video of drops firing from the print head nozzles. Experimental studies were also conducted to determine a suitable drop spacing (which depends on the ink and surface energy of the substrate). For example, in the examples described herein involving the printing of electrode arrays onto paper-based substrates, drop spacings were maintained between approximately 25-35 microns for all ink/paper combinations that were investigated.

Digital microfluidic array electrodes may be printed on a wide variety of substrates and surfaces according to the methods provided herein. For example, substrates that may be employed for the printing of digital microfluidic array electrodes include polymer films, such as polyester, polyimide, polyethylene terephthalate (PET) and polyethylene naphthalate (PEN); insulator substrates such as glass substrates; semiconductor substrates such as silicon; and composite substrates such as FR-4. Many of the inks described above have been found to be suitable for forming electrodes on such materials using inkjet printing.

It will be also understood that other printing methods may be employed in addition to inject printing, such as screen printing, flexography, gravure, offset lithography, microcontact printing, aerosol jet printing.

In order to be suitable for droplet manipulation by DMF, a substrate should be electrically insulating and have a low surface roughness to reduce contact line friction. The surface roughness of the hydrophobic/dielectric layer (which sits on top of the printed electrode layer) should be <1 micron to enable facile drop movement, so a constraint on the substrate surface roughness depends on the ability of the hydrophobic/dielectric layer to even out this underlying roughness. If the hydrophobic/dielectric layer is perfectly conformal, the surface roughness of the substrate should be less than approximately 1 micron, but some hydrophobic/dielectric coatings may enable rougher substrates.

In order to be suitable for the printing of electrodes, the substrate should also satisfy certain constraints on surface roughness and surface energy such that conductive inks adhere to the substrate, and that neighboring drops form contiguous, electrically conductive features.

It will be understood that specific constraints on substrate roughness and surface energy depend on the physical and chemical interactions between the ink and substrate. If the surface energy is too great, printed drops will not be confined to well-defined circular spots and can spontaneously wick outward in an uncontrollable manner. If the surface energy is too low, ink droplets can pool on the surface in an uncontrollable manner and may fail to contact neighboring printed drops resulting in gaps in the conductive features.

In some embodiments, the surface energy may be modified in order to facilitate printing of a given ink on a given surface. For any given ink and surface, there is a range of surface energies for which printed drops will dry to form well-defined circular spots. Any or all of the following methods may be employed to vary the surface energy in order to obtain conditions for printing electrodes.

In one embodiment, depending on the volume of these drops and the diameter of the resulting dried circular spots, the drop spacing can be adjusted such that the spots left by neighboring drops form continuous conductive features.

In another embodiment, the surface energy may be controlled by changing the chemical composition of the ink.

In other embodiments, the substrate, or a surface thereof, may be treated or modified prior to the printing of electrodes thereon. For example, the surface energy (or an equivalent or related measure, such as contact angle) can be controlled through modification of the surface, for example, via a chemical treatment or a plasma treatment (e.g. oxygen plasma treatment). Such an embodiment is illustrated in FIG. 1A, which shows an image of a test pattern of ink spot (dots spaced on a 254 micron grid) printed on glass and kapton, both with and without 5 min of oxygen-plasma treatment to show the effect of surface energy on the formation of droplets, in particular, their circular symmetry and their diameter. It is clear from this Figure that the surface properties may be modified in a controlled manner in order to obtain conditions suitable for the printing of electrodes thereon.

Figure 1B:
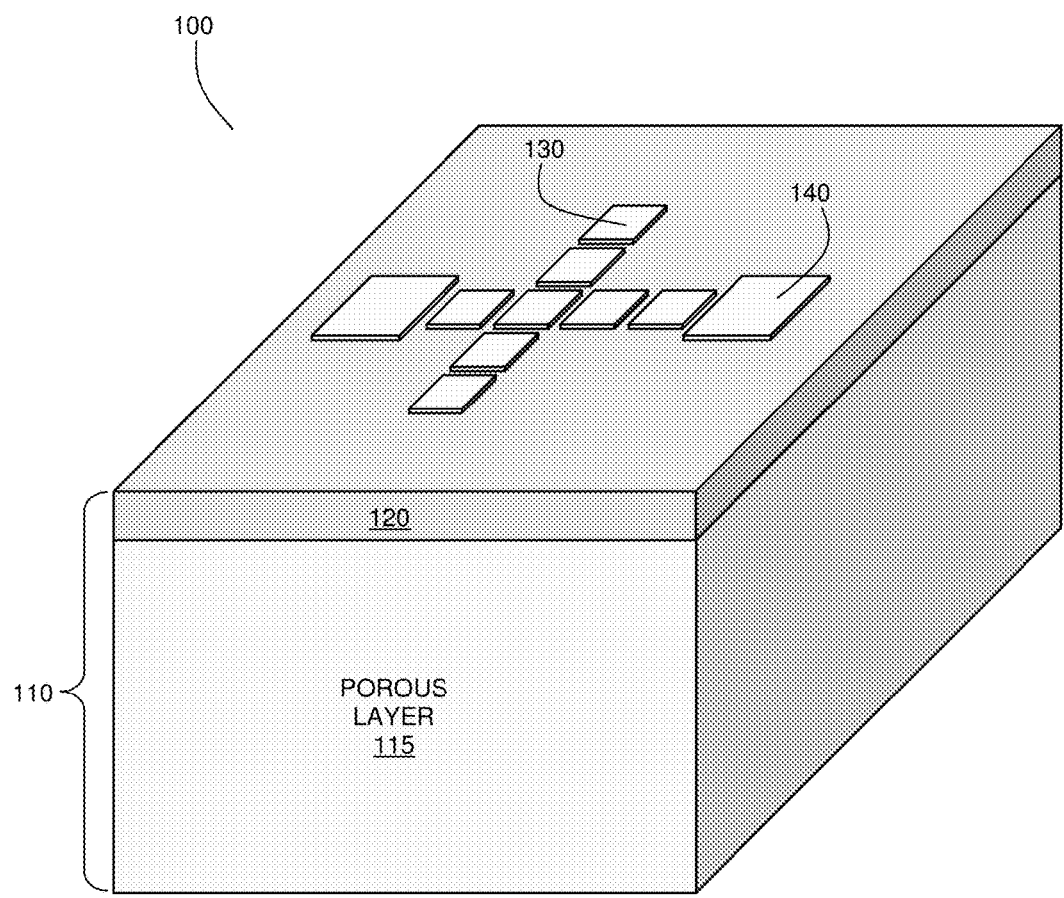
FIG. 1B is an illustration of an example array of digital microfluidic electrodes formed on a porous substrate.

In other embodiments, the substrate may be formed from a material that is porous or fibrous, and may include an additional barrier layer thereon that is formed with a suitable surface roughness and surface characteristics to support the printing of electrodes thereon. Referring to FIG. 1B, an example embodiment is shown in which an array of digital microfluidic electrodes is formed on porous substrate 110. In some embodiments, porous substrate 110 includes at least one porous layer 115 having barrier layer 120 provided thereon. Barrier layer 120 is a layer that is suitable for forming electrodes thereon, such as via printing. As described below, one or more additional layers may be provided in addition to barrier layer 120 in order to facilitate the formation of electrodes thereon.

The example array shown in FIG. 1B includes driving electrodes 130 and reservoir electrodes 140, which are provided on barrier layer 120. In one embodiment, each electrode may each be actuated by a dedicated contact electrode connected that is connected thereto via a conductive path (such contact electrodes and conductive paths are not shown in FIG. 1B. Electrodes 130 and 140 are provided with a size, spacing, and geometry that is suitable for droplet transport. Suitable parameters and geometrical ranges are described in detail below.

In some embodiments, the layer of porous material may be a fibrous material. The fibrous material may be formed from, naturally occurring cellulosic material. For example, the fibrous layer may be derived from a cellulosic pulp obtained from lignocellulosic material, such as wood, rags, and/or grasses.

In some embodiments, the fibrous layer may be one or more layers of paper, or a paper-based material. The paper or paper-based material may be formed from a paper making process, including, for example, chemical pulping methods such as, but not limited to, the Kraft process and the sulfite pulping process, mechanical pulping, and recycling methods. The paper may be any kind of paper that is suitable for forming electrodes thereon, such as printing and writing paper, wrapping paper, paper board, cardboard, cardstock, filter paper, and other specialty papers.

In some embodiments, the fibrous layer may be formed, at least in part, from a woven fibrous material. Examples of woven fibrous materials include textile materials, such as cloths and other fabrics formed in a sheet-like structure.

In some embodiments, the fibrous and/or porous layer may be formed, at least in part, from a synthetic material. Examples of synthetic fibrous materials include synthetic textile materials such as polyester fabric, filter materials formed from polymers, synthetic membrane materials, and lateral flow or western blot materials such as nitrocellulose.

In some embodiments, the at least an upper portion of the porous layer may comprise a porous material infiltrated with a solid or liquid substance. As described further below, a barrier layer is not necessarily required in such an embodiment.

In some embodiments, porous substrate 110 may comprise one or more a layers that is porous, but optionally not fibrous. Examples of non-fibrous, porous materials include Porous materials formed from sintered particles, etched materials, and self-assembled porous materials.

As noted above, porous substrate 110 includes a barrier layer 120 that is suitable for supporting an array of electrodes thereon. Barrier layer 120 may be formed from a wide array of different materials, according to various methods. For example, in some embodiments, barrier layer may be formed on a fibrous layer according to methods disclosed in US Patent Application No. 2011/0293851, filed by Bollstrom et al. on Feb. 2, 2006, which is incorporated herein by reference in its entirety.

One example of a barrier layer is a layer formed from barrier material comprising a mixture of a clay, such as kaolin, and a polymer, such as latex. One example implementation of such a barrier layer comprises of kaolin blended with approximately 30 pph ethylene acrylic acid copolymer latex. Such a layer has been shown to be suitable for the printing of conductive inks.

Figure 1C:
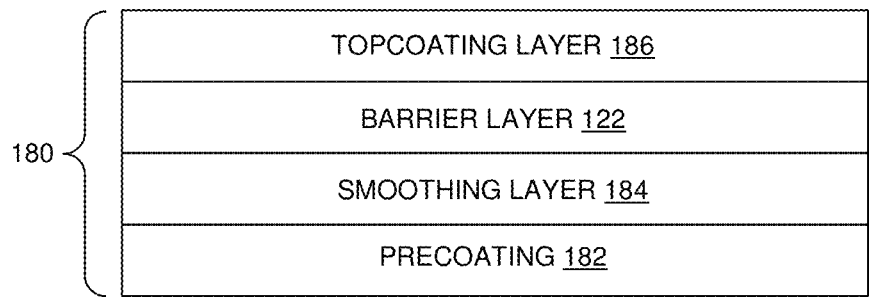
FIG. 1C shows an example implementation of an intermediate layer that is suitable for printing electrodes thereon.
Figure 1D:
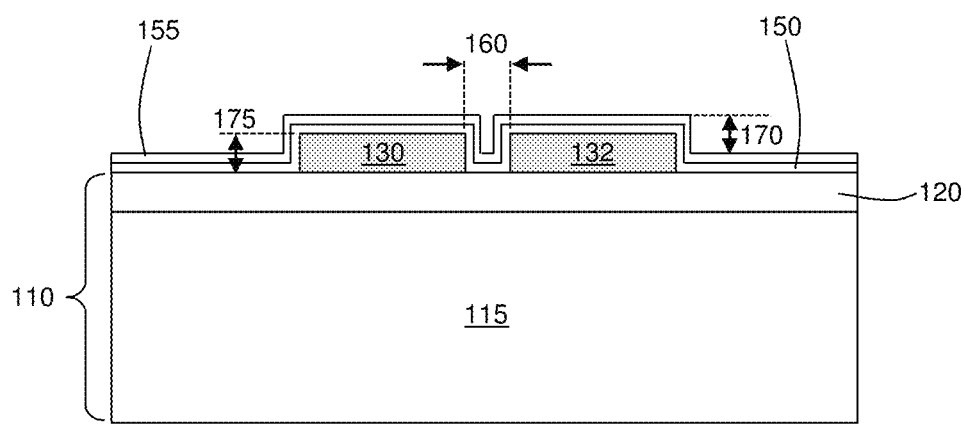
FIG. 1D shows a cross-sectional view illustration of an example digital microfluidic device.

FIG. 1C illustrates another example implementation of a set of intermediate layers 180 that may, in some embodiments, be employed instead of a single barrier layer. FIG. 1D illustrates an example and non-limiting embodiment of an intermediate layer suitable for the formation of electrodes thereon. Intermediate layer 180 includes precoating layer 182, smoothing layer 184, barrier layer 122, and topcoating layer.

As disclosed in US Patent Application No. 2011/0293851, precoating layer 182 may be formed, for example, from materials such as coarse mineral and/or pigment particles, such as ground calcium carbonate, kaolin, precipitated calcium carbonate or talc. The particles may typically have an average size of over 1 micron, measured by sedimentation, but the particle size of the mineral/pigment employed is not a critical factor.

Smoothing layer 184 may be formed, as noted in US Patent Application No. 2011/0293851, from fine mineral and/or pigment particles, such as calcium carbonate, kaolin, calcinated kaolin, talc, titanium dioxide, gypsum, chalk, satine white, barium sulphate, sodium aluminium silicate, aluminium hydroxide or any of their mixture. The mineral/pigment particles may typically have an average size less than 1 micron, measured by sedimentation, and in some embodiments, the thickness of the smoothing layer may be approximately 3-7 µm.

In some embodiments, barrier layer 122 may, as noted in US Patent Application No. 2011/0293851, comprise latex and mineral and/or pigment particles, which increase the surface energy of the barrier layer. Increase of the surface energy of the barrier layer improves the adhesion of the top coat layer to the barrier layer. The mineral/pigment particles employed may be the same as used in the top coat layer, i.e. kaolin, precipitated calcium carbonate (PCC), ground calcium carbonate (GCC), talc, mica or mixtures thereof comprising two or more of the said minerals/pigments. In some embodiments, the thickness of the barrier layer may be approximately 1-25 µm.

According to US Patent Application No. 2011/0293851, a thin top coat layer may be coated on the barrier layer. The top coat layer comprises mineral and/or pigment particles in order to improve the printability of the final substrate, and advantageously the top coat layer is as thin and smooth as possible. Typical minerals/pigments that may be used in the top coat layer are calcium carbonate, kaolin, calcinated kaolin, talc, titanium dioxide, gypsum, chalk, satine white, barium sulphate, sodium aluminium silicate, aluminium hydroxide or any of their mixture, kaolin or precipitated calcium carbonate (PCC). The thickness of the topcoat layer may lie within approximately 0.4-15 µm.

It is to be understood that the preceding examples of barrier layers, and additional layers that may be provided, are merely illustrative examples, and that other coatings or layers may be employed provided that they adhere to the porous layer and support the formation of electrodes thereon.

For example, an alternative type of substrate that may be employed for the printing of digital microfluidic arrays is paper substrates similar to commercial photo paper. Commercial photo papers, such as those made by Epson and HP, exhibit suitable surface properties (roughness and surface energy) comparable to the aforementioned barrier-coated substrates. Accordingly, it is expected that such paper substrates may be suitable for printing similar, and potentially even smaller, conductive features than those described above. It is noted that although the aforementioned multi-coat paper incorporating a barrier layer may be provided as a standard or typical paper substrate coated by a thin barrier layer, the photo paper appears to have a substrate that is perfused with a material that alters the hydrophobicity throughout all or at least an upper portion of the substrate (as opposed to merely a barrier layer formed on the top and bottom). For example, it has been observed that such photo paper substrates appear not to absorb water when they are laser etch them to various depths. Accordingly, in some embodiments, such infiltrated, fibrous substrates, having a suitable surface roughness, may be employed for printing digital microfluidic electrodes thereon without requiring a barrier layer on a surface thereof.

It will also be understood that although the preceding examples pertain to the use of printing methods for the formation of digital microfluidic electrodes on a porous substrate (comprising a porous layer and a barrier layer), in other embodiments, the electrodes may be formed on the barrier layer (or a suitable layer provided on the barrier layer) via other non-printing processes, such as electron-beam evaporation, sputtering, and other deposition methods, followed by a suitable subtractive fabrication method or step to produce the desired electrode features (for example, via photolithography and laser ablation).

Referring again to FIG. 1B, it will be appreciated that this example structure is rendered suitable for use as a DMF device via the formation of one or more dielectric and hydrophobic layers thereon. The addition of such layers is shown in the cross-sectional illustration provided in FIG. 1D. This example implementation shows a cross section of a porous-material-based DMF device, where porous substrate 110 (comprising porous layer 115 and barrier layer 120) supports driving electrodes 130 and 132. Driving electrodes 130 and 132, and the otherwise exposed top surface of barrier layer 120, are shown coated with a dielectric layer 150 (such as Parlyene) and a hydrophobic layer (such as Teflon). It will be understood that this embodiment is but one example of a DMF structure, and that in other embodiments, a single dielectric layer with a hydrophobic surface may be employed to coat the electrodes 130, 132 and barrier layer 120.

Figure 2:
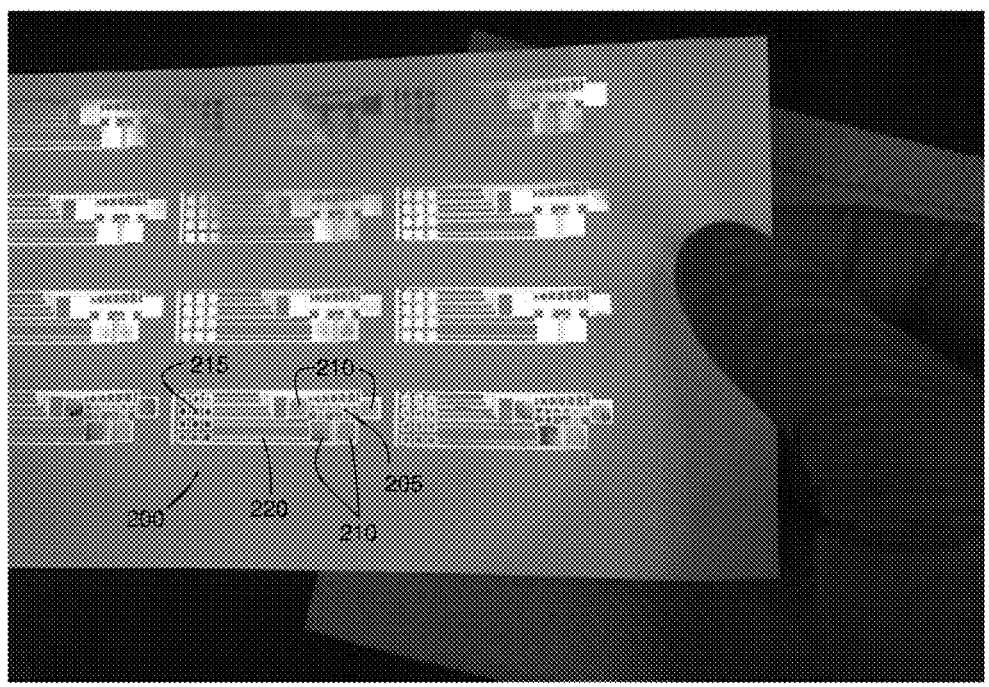
FIG. 2 shows a photograph of an array of digital microfluidic devices formed on a printed sheet of paper.

FIG. 2 shows a photograph of an array of digital microfluidic devices that were formed via the printing of electrodes on a paper substrate (having a barrier layer provided thereon). Each digital microfluidic device 200 includes driving electrodes 205 and reservoir electrodes 210. Contact electrodes 215 are connected to the driving and reservoir electrodes through conductive paths 220.

Figure 3A:
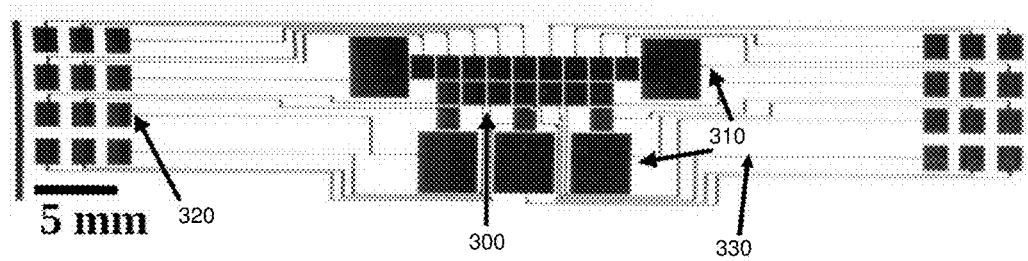
FIGS. 3A and 3B are illustrations of the electrode configurations of two different examples paper-based DMF devices, showing (A) design A and (B) design B.
Figure 3B:
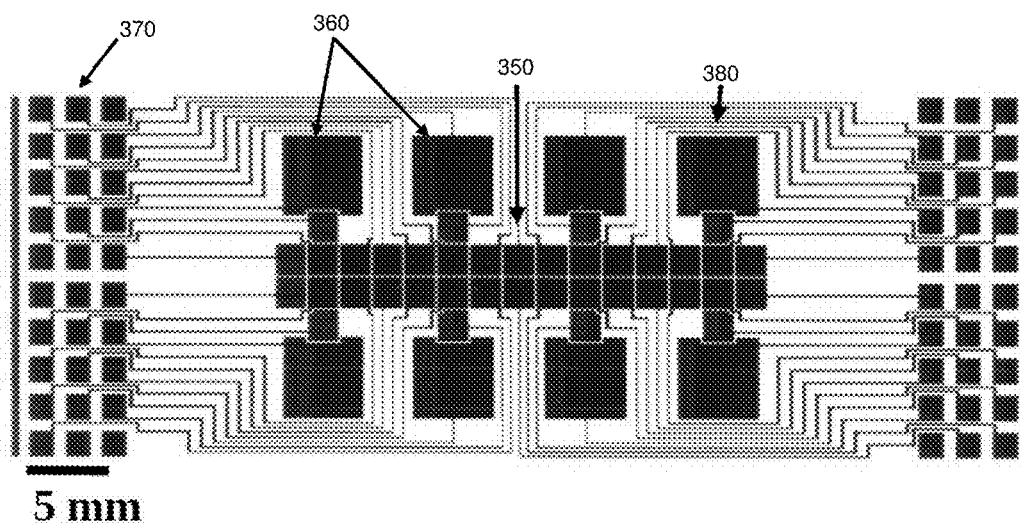

FIGS. 3A and 3B show illustrations of alternative example digital microfluidic devices that were printed via an inkjet printer, showing driver electrodes 300 and 350, reservoir electrodes 310 and 360, contact electrodes 320 and 370, and conductive paths 330 and 380.

The example DMF device shown in FIG. 1D may be employed as a one-plate DMF structure. In other embodiments, the example DMF device shown in FIG. 1D may be employed as the bottom (or top) plate of a two-plate DMF device. In such an embodiment, one or more spacers defining an intermediate gap, and a top plate may be provided having a similar structure to that of the device shown in FIG. 1D, for example, with a single global top plate electrode, or with a plurality of top plate electrodes. In other embodiments, a top plate may be provided in the form of a transparent substrate, such as a glass plate or polymer film having one or more conductive electrodes formed thereon (e.g. a transparent electrode formed from indium tin oxide, although non-transparent electrodes may also be used) provided thereon, and coated with a suitable hydrophobic layer and an optional dielectric layer. For example, such an embodiment may provide for a kit involving a reusable top plate, and disposable bottom plates.

It is also to be understood that, in a manner similar to that of traditional glass-based DMF devices, the DMF devices described herein should be able to operate in both open-air and oil-immersed environments. There may not need to be any modifications made to devices in order to operate in an oil environment. Like traditional DMF devices, the devices disclosed herein are expected to have similar advantages when operated with oil, including lower actuation voltages, elimination of droplet evaporation, decreased surface biofouling, and less stringent requirements for electrode separation and "trench" depth. Likewise, the DMF devices disclosed herein will experience the same disadvantages of operating in oil as glass devices, including unwanted extraction of analytes from droplets into the surrounding oil medium, incompatibility with oil-miscible liquids, and oil leakage from the device.

Referring again to FIG. 1D, an important feature for forming digital microfluidic devices is spatial resolution, which determines the minimum electrode separation that can be employed. The electrode spacing, henceforth referred to as the "inter-electrode trench width", can be an important parameter, as adjacent electrodes separated by large gaps (for example, larger than approximately 100 µm) can be problematic for drop movement [21]. The inter-electrode trench width is shown at 160 in FIG. 1D. In order to facilitate smooth drop movement, the inter-electrode trench width between electrodes should be small enough for the electric field originating in the neighboring (actuated) electrode to electrostatically interact with the leading edge of the liquid drop. This inter-electrode trench width should be between 5-100 µm, though sizes at the upper end of this range may cause problems with some liquids, smaller drops, etc. Smaller values of the inter-electrode trench width (for example, between approximately 5-50 µm) are preferable and should be sufficient for all workable conditions. Although this criterion is shown and described in an example pertaining to the formation of an electrode array on a porous substrate, it will be understood that this criterion, and the additional criteria described below, pertain also to DMF electrode arrays formed on non-porous substrates.

Figure 4:
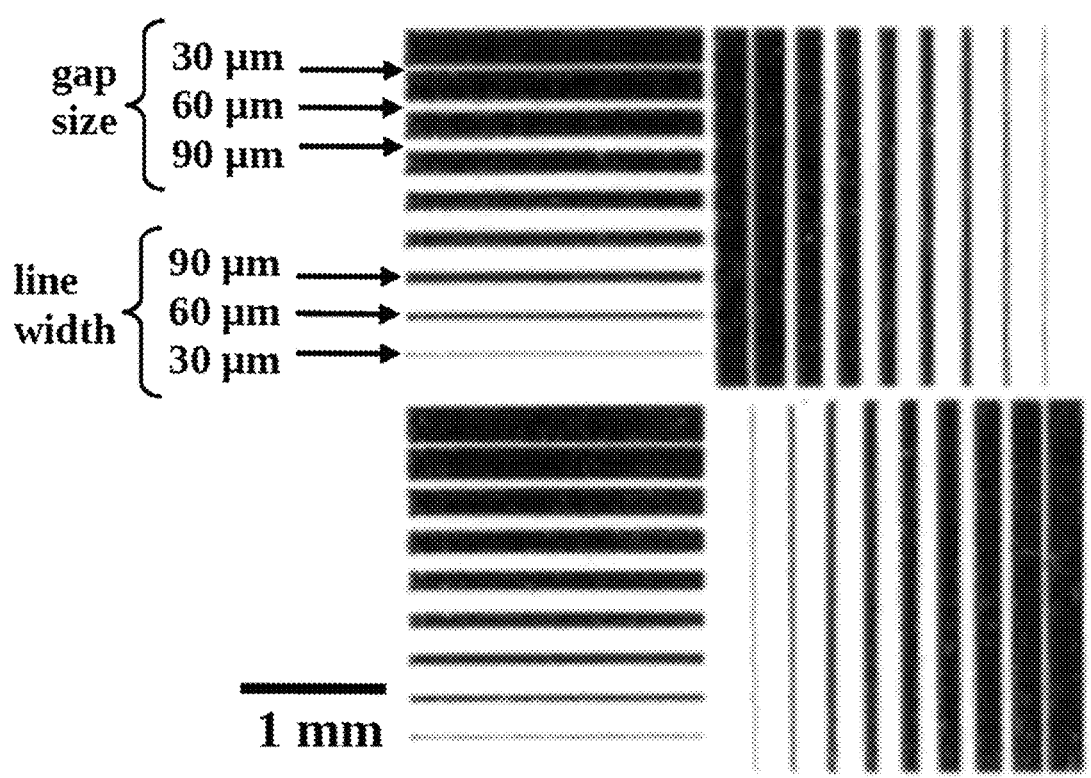
FIG. 4 is a photograph of a printed test pattern of electrodes on paper, showing gradients of line/gap widths in horizontal and vertical directions.

A resolution test pattern was performed to test the resolution of the inkjet printing method described above for an example paper-based substrate with a barrier layer. FIG. 4 demonstrates horizontal and vertical feature capabilities as small as 30 μm using this method, which is suitable for DMF. In general, it was observed that larger features had a lower probability of failure caused by electrical shorts or breaks. Accordingly, the driving electrodes employed in the paper-based DMF devices shown were formed with inter-electrode spacings of approximately 60-90 μm. It may be possible to further reduce this gap size by tuning the ink or surface properties of the barrier layer or an additional topcoating layer provided thereon.

Another geometrical parameter that has been found to have a significant impact on the droplet transport in DMF devices is the depth of the trench (e.g. gap or channel) formed between adjacent electrodes, which is henceforth referred to as "inter-electrode trench depth". The trench depth is shown at 170 in FIG. 1D, and this parameter is associated with the electrode height 175. In some embodiments, the inter-electrode trench depth should be less than 1 μm (depths of <500 nm are preferable).

It is instructive to contrast the values of the inter-electrode trench depth and width that are attainable via the methods disclosed herein with those that are attainable using PCB-based fabrication of DMF devices. It has been shown that due to the thickness of the copper layer of the PCB, the inter-electrode trench depth attainable for DMF devices fabricated on PCBs is greater than 15 μm. Such a deep inter-electrode trench depth can result in poor performance in droplet actuation and transport. Furthermore, typical PCB manufacturing processes cannot produce features smaller than 100 μm, which limits the inter-electrode trench width to greater than 100 μm, also resulting in performance problems due to relatively large spacing between adjacent electrodes.

It is noted that the preceding discussion of trench depths pertains to air-based DMF devices. When such devices are operated with an oil filler media, inter-electrode trench depths of up to approximately 10 μm and inter-electrode trench widths of up to approximately 150 μm may be sufficient.

Figure 9:
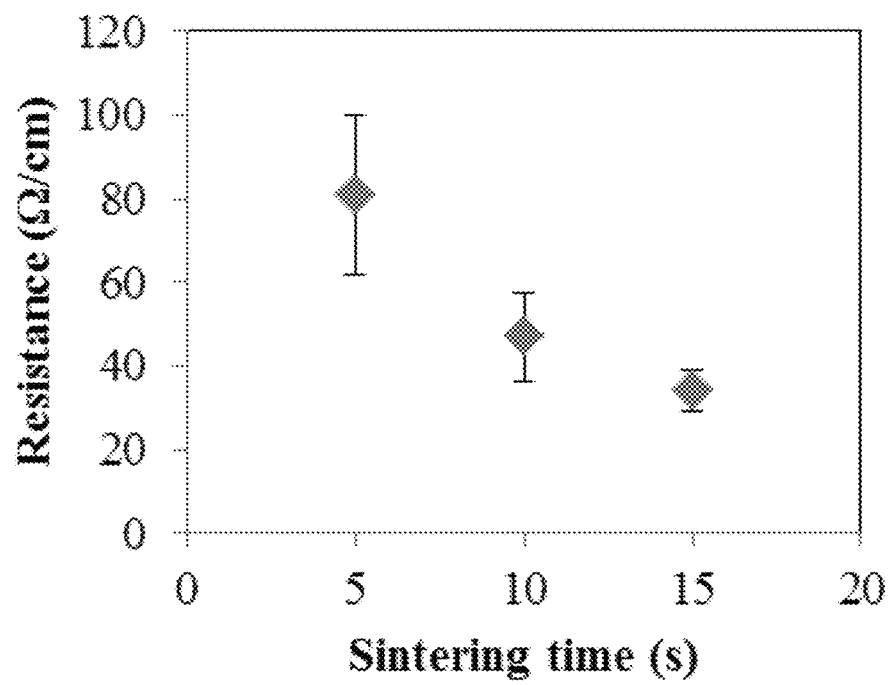
FIG. 9 is a plot showing the effect of sintering time on the resistance of 150 μm wide printed silver traces.
Figure 10:
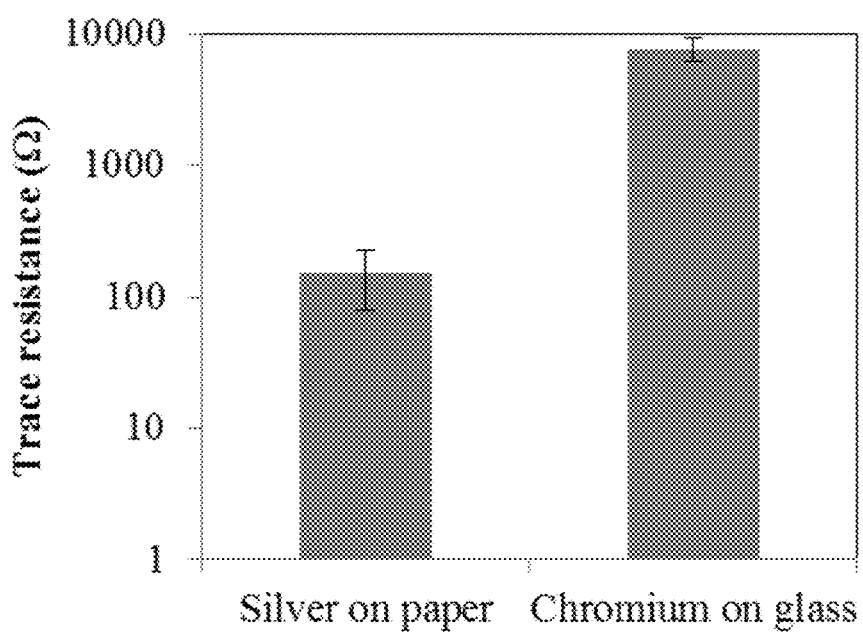
FIG. 10 shows the average resistance of all traces for DMF device design A fabricated by inkjet (silver on paper) and by standard photolithography (chromium on glass). Error bars are +/−1 standard deviation.

Another relevant performance feature is the conductivity of the electrodes and conductive paths. Thin electrodes with poor conductivity can result in Joule heating and/or unplanned voltage drops. As shown in FIG. 9, inkjet-printed trace resistance decreases as a function of sintering time, and, as shown in FIG. 10, these traces were found to have resistances that were 500 times lower than those for devices with identical designs fabricated by standard photolithographic methods (i.e., chromium on glass). The example devices described herein that were fabricated with a sintering time of approximately 10 s. FIG. 9 illustrates that other sintering times may also be employed to achieve low conductivity.

Another parameter that can impact the performance of a DMF device is surface topography, which occurs due to random variations in surface topography, and is often quantified as surface roughness. The electrostatic driving force used to manipulate drops on a DMF device is typically on the order of tens of μN. In order for the drop to move, this applied force must exceed the resistive forces that oppose drop motion. Resistive forces are composed of viscous drag (both within the drop and in the filler media: e.g., oil or air), and contact line friction, which is a property of the interactions between the device surface and liquid. In most cases (and especially in air-filled devices) the majority of the resistive force is due to contact line friction. Contact line friction can be reduced through the use of hydrophobic coatings, filling devices with oil, encapsulating drops in oil, etc.

Contact line friction is also affected by the surface roughness of the substrate. Decreasing surface roughness reduces contact line friction in general, and specifically, reducing the depth of the "trenches" between electrodes can prevent localized contact line pinning. The effects of surface topography for glass DMF devices bearing metal electrodes patterned by photolithography (often used in academic labs) have been negligible; while in contrast, the performance of DMF devices formed by PCB fabrication can be severely compromised by topography [21]. Indeed, the smooth surface (surface roughness<100 nm) measured for devices fabricated according to the methods disclosed herein is a result of the barrier coating and surface treatments applied to the paper, as compared to a surface roughness of printed circuit boards (PCBs) which is typically greater than 1 μm. Accordingly, in some embodiments, the surface roughness of a printed digital microfluidic device is less than approximately 1 μm, less than approximately 500 nm, or less than approximately 100 nm.

Figure 11A:
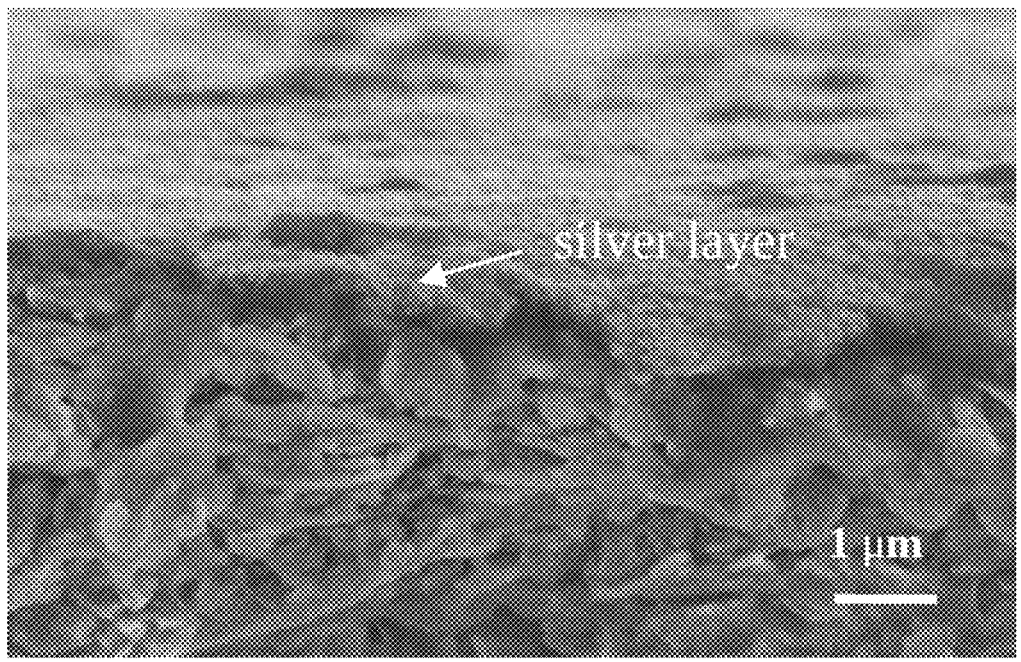
FIGS. 11A and 11B are SEM images showing cross-sectional views of a paper device with a printed silver electrode at two different magnifications.
Figure 11B:
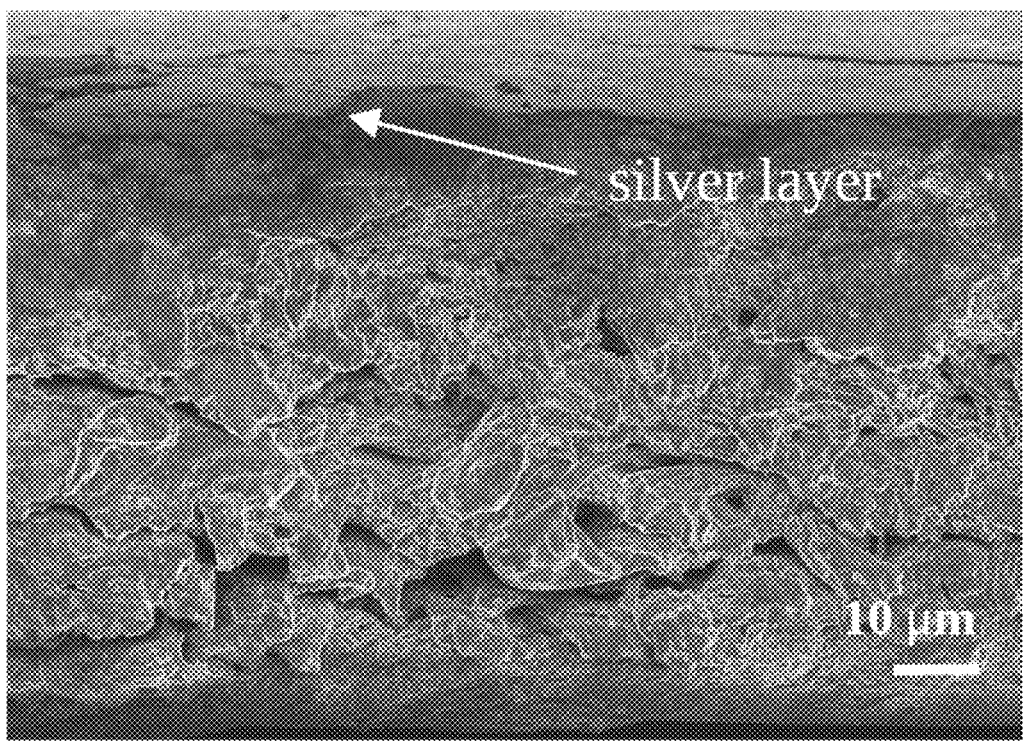

As shown in FIGS. 11A and 11B, the surface roughness of the silver layer formed on the barrier layer is very for the example devices fabricated as described herein. This is consistent with the droplet velocity measurements shown in FIG. 12B, which closely approximate those obtained via Embodiments provided herein may be employed to provide a wide array of DMF devices for conducting various droplet-based protocols, such as droplet-based assays, using electrodes printed on a porous substrate. For example, the embodiments disclosed herein may be adapted to implement a complex, multistep assays that are not currently achievable using existing paper microfluidics platforms.

Furthermore, in some embodiments, DMF devices may be formed on a porous substrate comprising a hydrophilic layer (e.g. a hydrophilic fibrous and/or porous layer) that may be adapted to incorporate one or more channel-based microfluidic features or elements therein, thereby providing a hybrid DMF-microchannel device. Such hybrid devices may be employed, for example, to utilize DMF for complex drop manipulation combined with more traditional capillary-flow based paper-microfluidic techniques.

Figure 5:
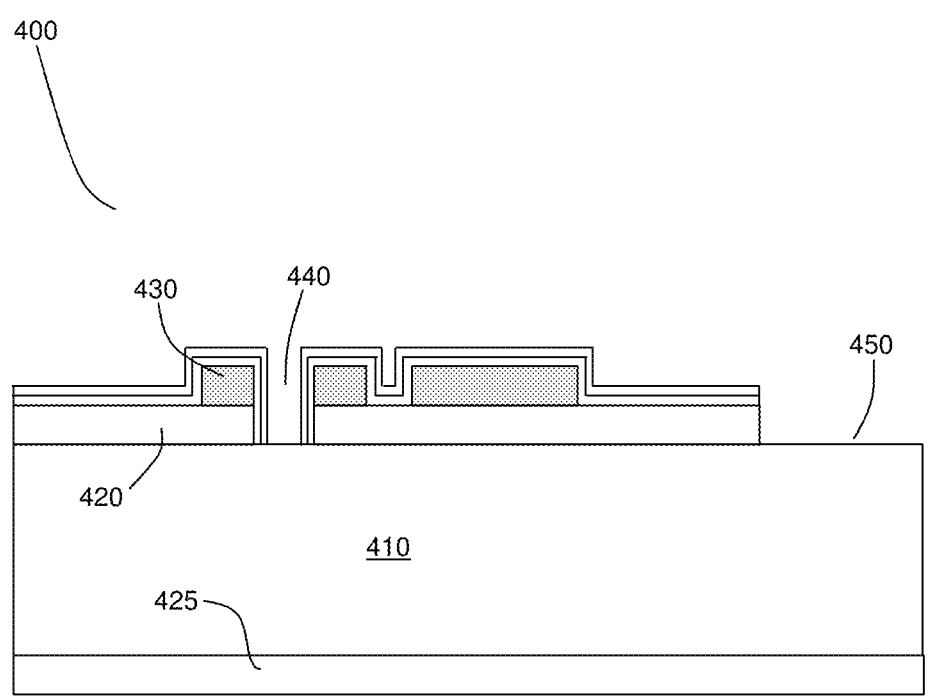
FIG. 5 shows a cross-sectional view illustration of an example digital microfluidic device having a lower barrier layer and an extended porous layer.

FIG. 5 shows an example DMF device 400 which is obtained by modifying the DMF device of FIG. 1D to allow for fluid communication between the DMF layer and the underlying hydrophilic layer 410. A lower barrier layer 425 has been added to confine fluid flow within hydrophilic layer 410, and barrier 420 has been exposed in two locations. At 440, an aperture has been formed through electrode 430 and through barrier layer 420. At 450, barrier layer 420 has been removed to expose the underlying hydrophilic layer, for example, to provide access or visibility to a microfluidic channel formed therein.

Figure 6A:
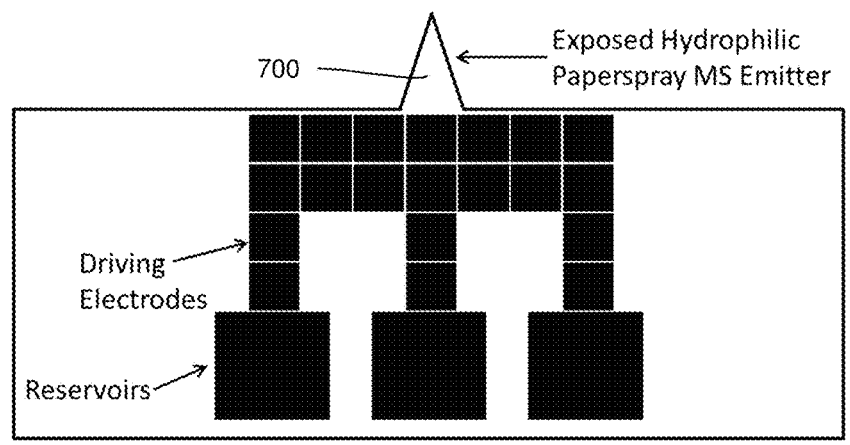
FIG. 6A shows an illustration of an example hybrid paper-based DMF device with integrated paperspray mass spectroscopy (MS) emitter.
Figure 8:
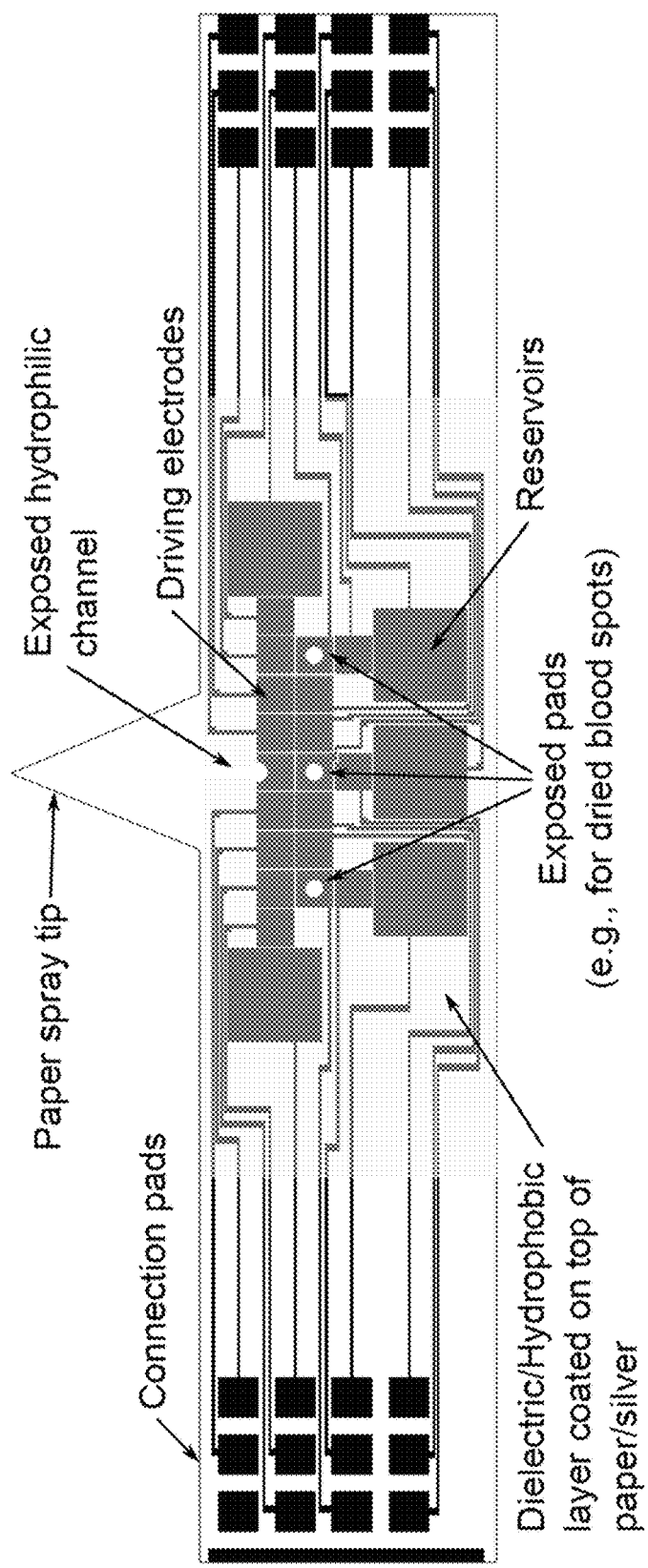
FIG. 8 shows another illustration of an example hybrid paper-based DMF device with integrated paperspray mass spectroscopy (MS) emitter.

Examples of capillary-flow based paper microfluidic techniques that may be incorporated include, but are not limited to, electrospray (e.g. paperspray) mass spectrometry emitters including an exposed portion of the hydrophilic substrate 700 formed as a tip, as shown in FIG. 6A. Another example of such a device is shown in FIG. 8. Electrospray mass spectrometry emitters require a sharp tip to spray from, and an external high voltage power source for the spray potential. The triangle shape of the electrospray (e.g. paperspray) emitter may be cut at the edge of the DMF device after the removal of the top barrier layer (such as region 450 shown in FIG. 5) or by generation of an access hole through the barrier layer to the hydrophilic paper underneath (such as at 440 in FIG. 5). The spray voltage may be applied via a conductive clip connected to the wetted paperspray emitter, or alternatively, through an electrode printed directly on the hydrophilic paper of the paperspray emitter.

Figure 6B:
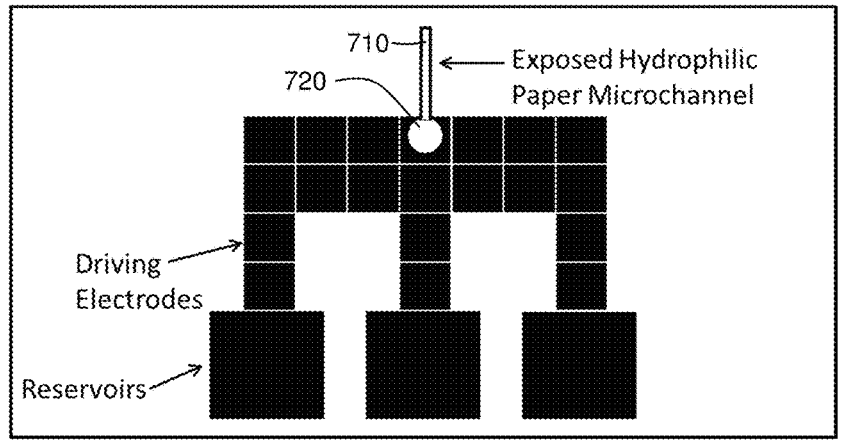
FIG. 6B is an illustration of an example hybrid paper-based DMF device with an integrated paper microchannel.

Other examples of hybrid devices include hybrid DMF-microchannel and/or lateral flow devices, where a DMF array is provided on a hydrophilic substrate (on a barrier layer as described above), and wherein a portion of the barrier layer is removed to expose the underlying hydrophilic layer that is configured as a microchannel or a lateral flow membrane, thereby allowing contact and adsorption of the droplets into the hydrophilic layer and directed flow within the hydrophilic layer. In one embodiment, a lateral flow channel could be provided as a broad channel, as in conventional lateral flow devices. In another embodiment, the channel could be a microchannel confined by hydrophobic walls (e.g. with a diameter of 1 mm or less), as in paper-based microfluidic channels. The lateral flow channel or microchannel could incorporate dried and/or immobilized reagents for performing assays such as colourimetric assays. FIG. 6B shows an example implementation of a microchannel-based device that employs a confined microchannel 710 for lateral flow and/or separations, which is accessible through aperture 720.

Figure 6C:
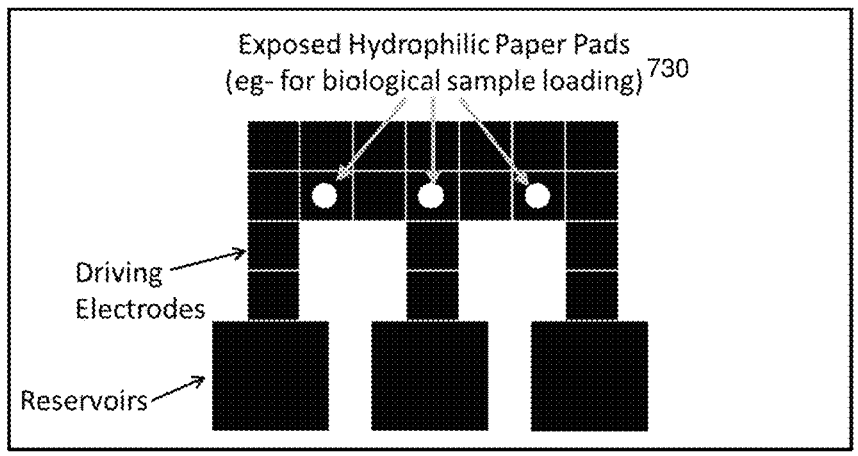
FIG. 6C is an illustration of an example hybrid paper-based DMF device with integrated hydrophilic paper pads for biological sample loading.

In another example embodiment, shown in FIG. 6C, a DMF device may be adapted to expose specific regions of the hydrophilic layer in order to provide hydrophilic pads 730. Hydrophobic walls may be formed surrounding the exposed hydrophobic regions in order to confine liquid therein and limit the absorption capacity of the hydrophilic pads. Such an embodiment may be employed for biological sample loading, such as loading samples onto a digital microfluidic device, thereby addressing the chip-world problem. For example, the hydrophilic pads could be used to provide dried blood spots (DBS) or dried urine spots (DUS). In this case, the sample can be completely integrated into the device, making sample collection prior to processing and analysis much easier. One or more pads may also or alternatively be employed to provide dried reagents for assays. As shown in the Figure, the hydrophilic pads are be oriented within DMF electrodes to facilitate facile droplet movement over the pads, such as for extraction, chemical derivatization, and other processing steps.

In one embodiment, a DMF device could be fully assembled (e.g. top and bottom plates attached with either a partial or full gasket enclosing the electrode array) and blood or urine samples could be introduced through hydrophilic pads on the bottom of the device (and/or top of the device is such features are formed in the top plate), as the hydrophilic pads would effectively act as vias employing capillary action. Such an embodiment would be beneficial in that it would prevent the working, hydrophobic surfaces of the device from getting scratched, dirty, or otherwise contaminated during the loading of the device with samples or reagents.

Although each hybrid platform may serve a unique function, the device format for each embodiment generally includes (i) a region where the top barrier layer is removed to reveal the hydrophilic substrate underneath, and/or (ii) a region where a hole or other aperture is provided through the top barrier layer to the hydrophilic substrate such that droplets can travel to and wick into the substrate through this hole.

In yet another embodiment, a portion of the barrier layer is removed to expose the underlying hydrophilic layer, which may act as a waste reservoir for a DMF array formed on the barrier layer. For example, if an electrode is placed nearby or adjacent to the exposed region, or, for example, if a portion of the electrode is also removed to expose the underlying hydrophilic layer, then a droplet contacting the electrode could or would flow into the underlying hydrophilic layer, thereby acting as a buried waste reservoir. In some embodiments, the entire underlying layer could be available as a buried waste reservoir, while in other embodiments, one or more buried waste reservoirs could be defined via hydrophobic walls within the underlying hydrophilic layer. In another embodiment, the hydrophilic portion of the device, acting as a waste reservoir, could be placed in physical contact with an external absorbent pad for further increasing the waste storage capacity.

Figure 7:
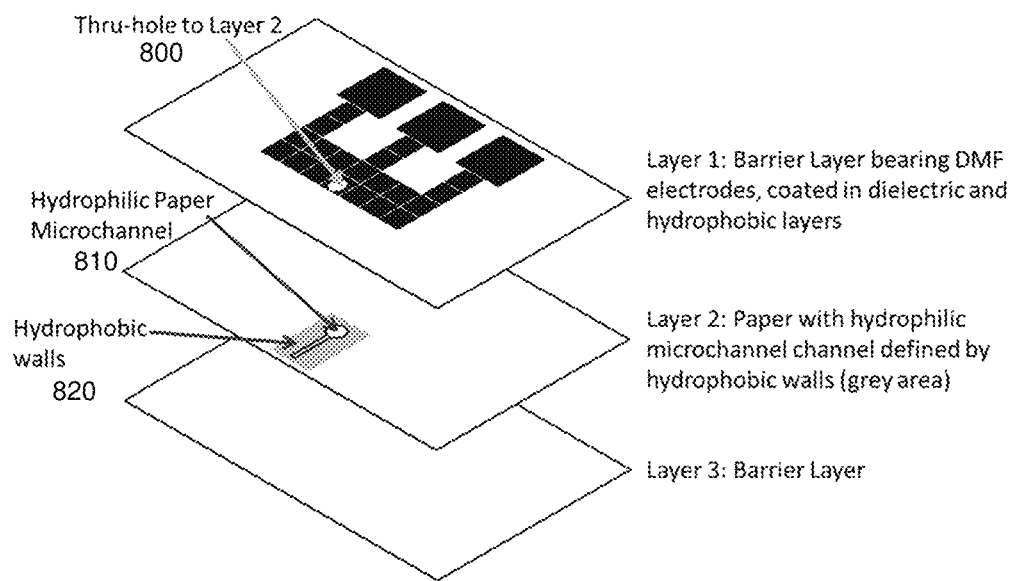
FIG. 7 is a schematic showing three layers of an example hybrid DMF device formed on a porous substrate, showing how samples can travel from the top layer (barrier layer bearing the working DMF electrodes) to the hydrophilic substrate underneath.

FIG. 7 shows an exploded diagram illustrating the modifications made to the various layers of an example hybrid device. The top barrier layer is removed to expose the hydrophilic substrate underneath in a specific location on the device at 800, thereby forming a thru-hole to the hydrophilic layer. In one embodiment, the barrier layer may be removed before application of the dielectric and hydrophobic layers of the DMF device, and the area will be masked to prevent deposition of dielectric and hydrophobic layers on the exposed bare paper. The barrier layer may be selectively patterned or removed completely in the desired area. This may be achieved, for example, mechanical removal, laser etching or chemically etching (such as wet chemical etching by acid, or oxygen reactive ion etching). As shown in the Figure, the geometry of the channel 810 or pad in the hydrophilic paper may be defined by hydrophobic walls 820 or a hydrophobic boundary region. It will be understood that the hydrophilic walls may be created using several methods including, but not limited to, applying wax to the hydrophilic material, in the desired hydrophobic area, and photolithographic patterning of hydrophobic areas (e.g. using SU-8 photoresist). In another embodiment, the channel may be formed by mechanically removing the hydrophilic material from the area surrounding the channel to create a "cut out" of the channel.

Although the preceding example embodiments of hybrid devices have been presented separately, it will be understood that two or more of these hybrid embodiments may be integrated onto a single device. For example, a single hybrid device may include hydrophilic pads for sample loading and a paperspray emitter for MS analysis (extraction and analysis of drugs from dried blood spots), and any other combination of these or other hybrid embodiments.

In another embodiment, hydrophobic features, such as spots or channels, may be formed on the surface of a non-porous substrate, and integrated with a printed array of DMF electrodes. For example, non-porous substrates with hydrophilic features have been recently demonstrated (e.g., polymer films). The method of Tian et al. [Tian, Junfei, Xu Li, and Wei Shen. "Printed Two-dimensional Micro-zone Plates for Chemical Analysis and ELISA." Lab on a Chip 11, no. 17 (Aug. 8, 2011): 2869-2875. doi:10.1039/C1LC20374F.] involves inkjet printing of a UV-curable varnish onto which fine powders of cellulose or other materials are applied. After UV-curing, the powder particles are fixed by the cured varnish, leading to the formation of porous, hydrophilic features.

Accordingly, in one embodiment, hydrophilic elements could be fabricated on a substrate having a DMF array thereon (e.g. formed via printing, as described above) using such methods, where the DMF substrate need not be porous or contain a buried hydrophilic layer. Such hydrophilic elements could be integrated with the DMF array to provide a hybrid device (e.g. printed DMF electrodes with integrated dried blood spot zones, lateral flow channels, waste reservoirs, and/or electrospray features).

In yet another embodiment, one or more sensor electrodes may be printed on a substrate with a digital microfluidic array, such as, but not limited to, electrodes for electrochemical detection and/or impedance sensing.

The following examples are presented to enable those skilled in the art to understand and to practice embodiments of the present disclosure. They should not be considered as a limitation on the scope of the disclosure, but merely as being illustrative and representative thereof.

EXAMPLES

Example 1

Materials and Reagents

Unless otherwise specified, reagents were purchased from Sigma-Aldrich (Oakville, ON). Deionized (DI) water had a resistivity of 18 MΩ·cm at 25° C. Pluronic L64 (BASF Corp., Germany) was generously donated by Brenntag Canada (Toronto, ON). Multilayer coated paper substrates for device printing were graciously provided by Prof. M. Toivakka of Åbo Akademi University, Finland [27]. On-chip reagent solutions were either obtained from vendors or were custom-made in-house. Reagents from vendors include rubella IgG standards and rubella virus coated paramagnetic microparticles from Abbott Laboratories (Abbott Park, Ill.), and SuperSignal ELISA Femto chemiluminescent substrate, comprising stable peroxide (H2O2) and Luminol-Enhancer solution, from Thermo Fischer Scientific (Rockford, Ill.). Custom DMF-compatible wash buffer and conjugate diluent were prepared as described previously [24,26]. Prior to use, rubella IgG standards diluted in Dulbecco's Phosphate-Buffered Saline (DPBS) containing 4% Bovine Serum Albumin (BSA) and chemiluminescent substrate were supplemented with Pluronic L64 at 0.05% and 0.025% v/v, respectively. Conjugate working solutions were formed by diluting horse-radish peroxidase (HRP) conjugated goat polyclonal Anti-Human IgG (16 ng/mL) in conjugate diluent. The microparticle working suspension was formed by pelleting, washing, and resuspending microparticles in Superblock TBS from Thermo Fischer Scientific (Rockford, Ill.) at "1.5×108 particles/mL.

Example 2

DMF Device Fabrication

Paper DMF devices were formed by inkjet printing arrays of silver driving electrodes and reservoirs connected to contact pads. FIGS. 1A and 1B contain representative photographs of such substrates; as shown, two different designs were used. Design A includes 5 reservoir electrodes (4.17× 4.17 mm) and 19 driving electrodes (1.65×1.65 mm) and Design B includes 8 reservoir electrodes (5.6×5.6 mm) and 38 driving electrodes (2.16×2.16 mm). In practice, each paper substrate formed a device bottom plate, which was joined with a conductive top plate to manipulate 400-800 nL drops sandwiched between them.

DMF bottom plates were formed by printing electrode patterns onto paper substrates using a Dimatix DMP-2800 inkjet printer (FUJIFILM Dimatix, Inc., Santa Clara, Calif.) and SunTronic U6503 silver nanoparticle-based ink according to the datasheet provided by the manufacturer. After printing, the substrates were sintered using a 1500 W infrared lamp [28] at a distance of ~1 cm for 10 s.

Design A was also fabricated with chromium-on-glass substrates as described previously [22]. As described further below, design B was used for the rubella IgG immunoassay assay, while design A was used for all other experiments.

To date, more than one hundred working paper-based DMF devices have been fabricated. The devices are inexpensive and fast to make; the cost of ink and paper is less than $0.01 per device and designs A and B require approximately 1 and 2 minutes each to print. It is to be understood that these costs and times are based on the printing of single devices using a single printer, and that it is expected that both cost and speed will improve as the printed electronics field matures and/or if these methods are scaled to larger production runs. For example, commercial conductive inks are still relatively expensive when ordered in small quantities, e.g., ~$30/mL, and typical office inkjet printers (which rely on the same piezoelectric principle) have >100 nozzles compared to <6 that were practical to use simultaneously in this example. Since printing time is inversely proportional to the number of nozzles, it is expected that in the future it may be possible to reduce this time to just seconds per device.

Paper substrates were affixed to glass slides to ease handling. Teflon thread seal tape (McMaster-Carr, Cleveland, Ohio) was wrapped around the electrical contact pads to prevent them from being covered by subsequent insulating layers. Both types of substrates (glass and paper) were coated with 6.2 µm Parylene-C in a vapor deposition instrument (Specialty Coating Systems, Indianapolis, Ind.) and ~50 nm of Teflon-AF 1600 (DuPont, Wilmington, Del.) by spin-coating (1% wt/wt in Fluorinert FC-40, 1000 rpm, 30 s) and postbaking at 160° C. for 10 min. Indium-tin-oxide (ITO) coated glass plates (Delta Technologies Ltd., Stillwater, Minn.) were also coated with 50 nm of Teflon-AF (as above) for use as device top plates. Top and bottom plates were joined by stacking two pieces of double-sided tape (~80 µm ea.), resulting in a unit drop volume (covering a single driving electrode) of ~440 nL (Design A) and ~750 nL (Design B).

Example 3

Conductivity of Glass and Paper-Based DMF Devices

The conductivity across 2 cm long/150 µm traces of ink-jet printed silver on paper (after sintering for 5, 10, or 15 s) was measured with a Fluke 179 True RMS Digital Multimeter; 9 traces were evaluated for each condition (3 on three separate devices). The resistance between contact pads and driving electrodes was measured for all electrodes of Design A for 3 paper and 3 chromium on glass devices. As shown in FIG. 9, inkjet printed trace resistance decreases as a function of sintering time, and, as shown in FIG. 10, these traces were found to have resistances that were 500 times lower than those for devices with identical designs fabricated by standard photolithographic methods (i.e., chromium on glass).

Example 4

Surface Roughness of Glass and Paper-Based DMF Devices

Scanning electron micrography (SEM) was used to evaluate the surface shape of the paper devices used here (FIGS.

11A and 11B). As shown, the thickness of the silver layer on inkjet-printed paper devices is <500 nm, which is much thinner than the 10-30 μm thick electrodes commonly found on devices formed from PCBs (note that deep "trenches" between electrodes on PCB-based DMF devices have been reported be problematic for drop movement [19-21]). Atomic force microscopy (AFM) was used to evaluate surface roughness, revealing a surface roughness ($R_a$) of $R_a \approx 250$ nm for bare silver on paper substrates, and $R_a < 100$ nm for silver-paper substrates after deposition of Parylene-C and Teflon. These values are between one and two orders of magnitude smaller than those reported for PCB DMF devices [18-20].

SEM images were acquired with a S-3400N Variable Pressure SEM (Hitachi High Technologies America, Inc., Schaumburg, Ill.) in secondary electron mode with an accelerating voltage of 5 kV. Surface roughness estimates are based on the arithmetic average of absolute height values across a 125×125 μm window (512×512 samples) measured in air with a Digital Instruments Nanoscope IIIA multimode AFM (Bruker Nano Surface, Santa Barbara, Calif.) in tapping mode (1 Hz scan rate). All images were subjected to a zero-order flatten and 2nd-order plane fit filters prior to analysis.

The most straightforward measure of the effects of surface topography on DMF performance is to evaluate the actuation of individual drops. Devices were interfaced through pogo-pin connectors to one of two variations of the open-source DropBot drop controller, either with [24] or without [22] integrated magnetic control. Drops were controlled and velocities were measured using an impedance-based feedback circuit [22].

Figure 12A:
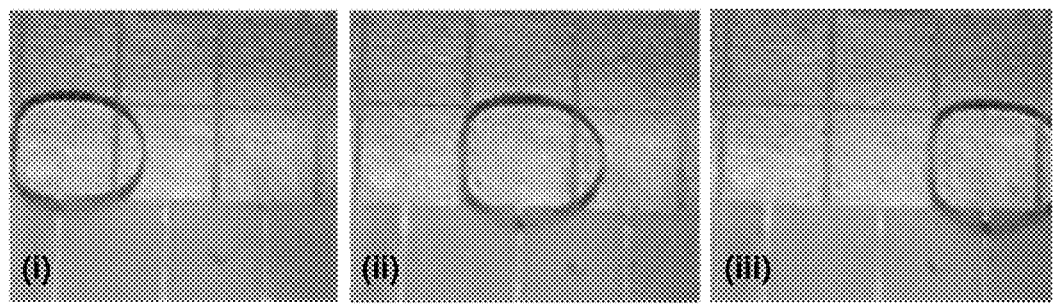
FIG. 12A is a series of video frames demonstrating translation of a drop of water on a paper device, as shown in panels (i) to (iii).
Figure 12B:
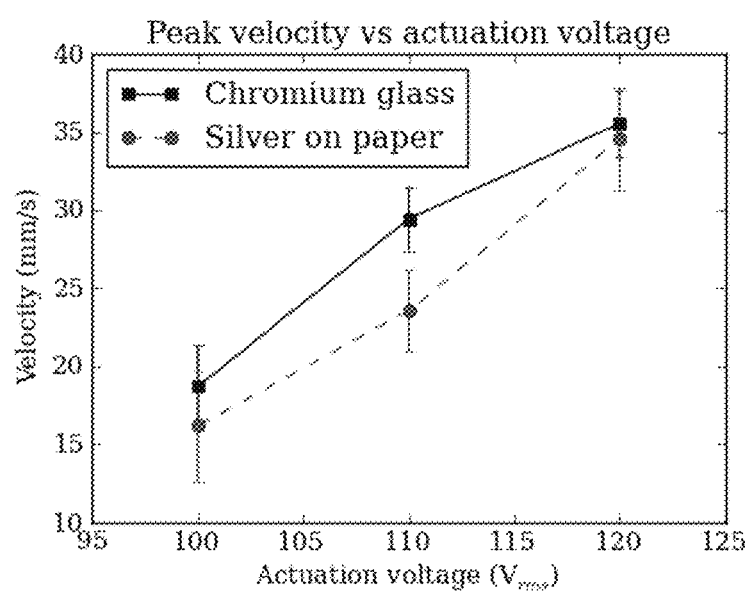
FIG. 12B plots peak velocities of water drops on a paper-based DMF device (circles) relative to those on a standard device fabricated by photolithography (squares). Error bars are +/−1 standard deviation.
Figure 13A:
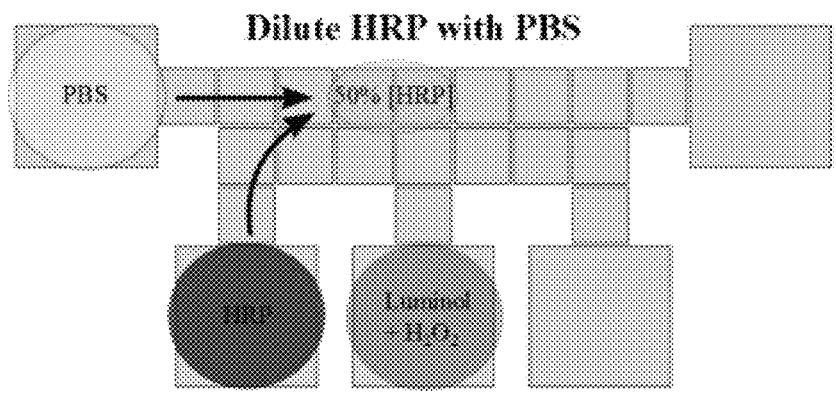
FIGS. 13A-13E schematically illustrate the steps involved in performing an example homogeneous chemiluminescence assay on a paper DMF device though on-chip serial dilution of HRP mixed with Luminol/H2O2.
Figure 13B:
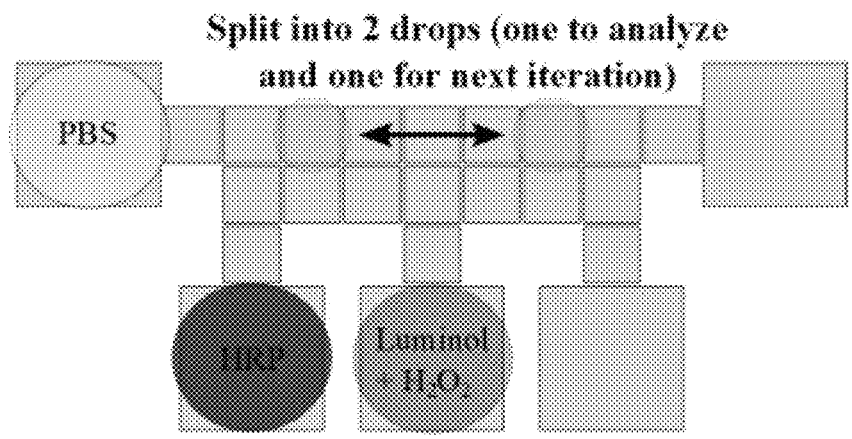
Figure 13C:
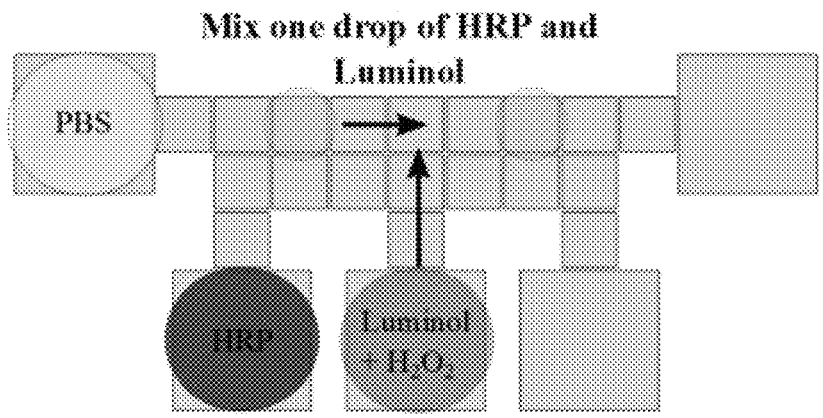
Figure 13D:
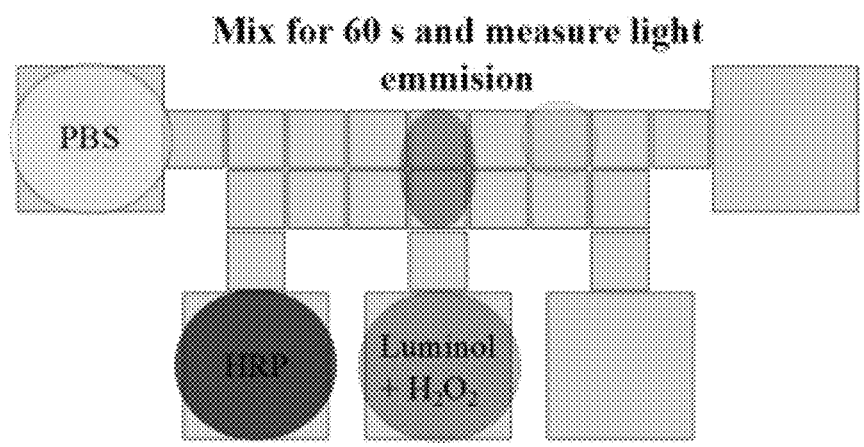
Figure 13E:
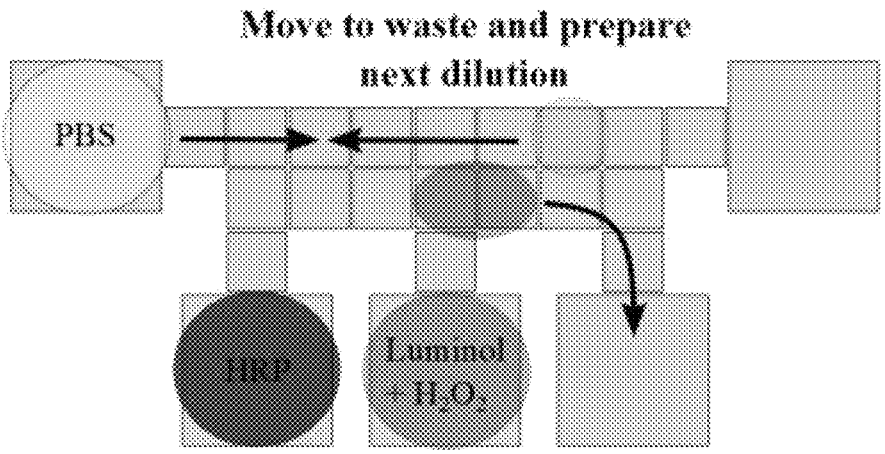

FIGS. 12A and 12B demonstrate the movability of water drops on paper devices. The instantaneous velocities of drops of water were measured by impedance sensing [22] and the data suggests that the performance of paper DMF devices is comparable to that of glass devices formed by photolithography.

Example 5

Demonstration of Homogeneous Chemiluminescent Assay Using Paper-Based Digital Microfluidic Device Drops of HRP standard (100 μU/mL in DPBS supplemented with 0.05% v/v L64) and drops of wash buffer were dispensed from reservoirs, mixed, and merged to form a dilution series (1×, 2×, 4×). One drop of SuperSignal chemiluminescent substrate was then dispensed, mixed, and merged with each diluted drop of HRP, and the pooled drop was mixed for 40 seconds, driven to the detection area, and the emitted light was measured after 2 minutes with an H10682-110 PMT (Hamamatsu Photonics K.K., Hamamatsu, Japan). Each condition was repeated 3 times.

Figure 14:
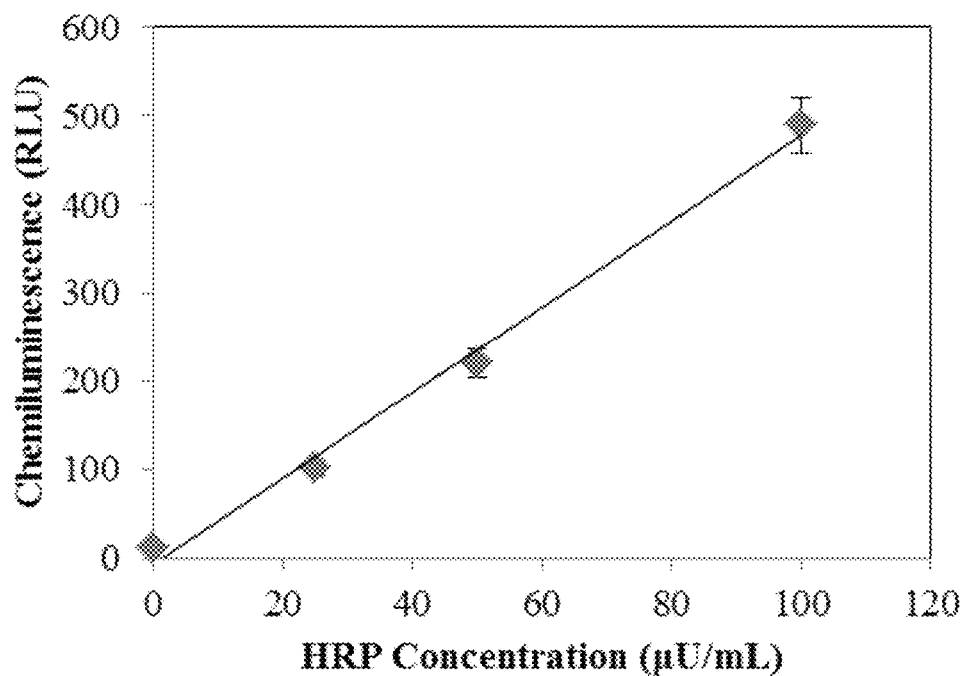
FIG. 14 is a calibration curve (n=3) measured for the example homogeneous chemiluminescence assay. Error bars are +/−1 standard deviation.
Figure 15:
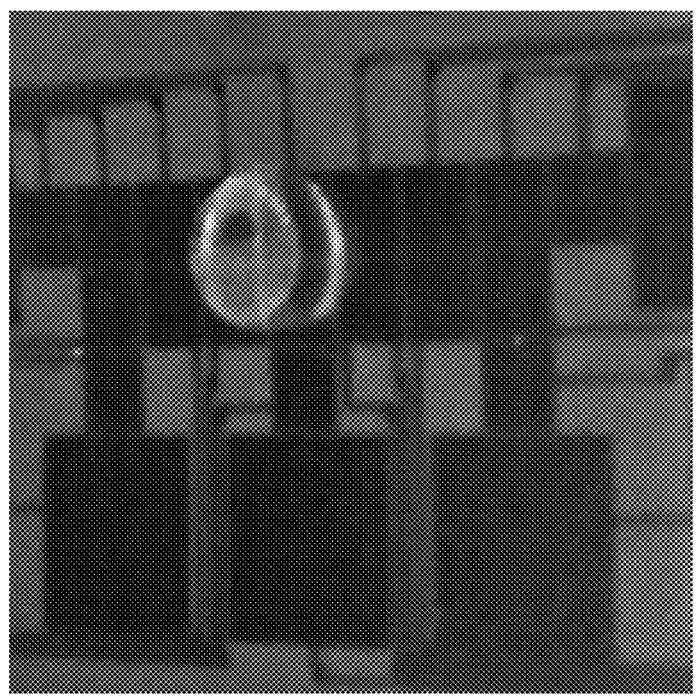
FIG. 15 is an image of an example device after performing the step shown in FIG. 13D, shown with top plate removed for visualization.

Two tests were developed to probe the capacity of paper DMF devices for performing complex, multi-step assays. As a first test, the ability to generate an on-chip serial dilution and calibration curve for a homogeneous chemiluminescence assay was explored: horseradish peroxide (HRP) mixed with luminol/H2O2. As depicted in FIGS. 13A-E, this experiment requires 63 discrete steps: 27 dispense, 18 mix, 6 split, and 12 measure. From a total of three initial pipette steps, a four-point calibration curve can be created. Despite this complexity, the assay was straightforward to implement reproducibly on paper DMF devices (FIG. 14, R2=0.993). FIG. 15 shows a photograph of a device after step 4 with top plate removed for visualization. The complexity of this assay is such that it would likely be difficult or perhaps impossible to perform on a capillary-driven paper device.

Example 6

Demonstration of Rubella IgG Immunoassay Using Paper-Based Digital Microfluidic Device As a second test to probe the feasibility of complex assay development using paper DMF and to demonstrate the suitability of these devices for low-cost diagnostic testing, it was chosen to implement a rubella IgG sandwich ELISA. Rubella, also known as German measles, is a disease caused by the rubella virus. Although it poses few complications when acquired post-natally, congenital rubella syndrome can cause of serious developmental defects including blindness, deafness and termination of pregnancy [23].

Figure 16:
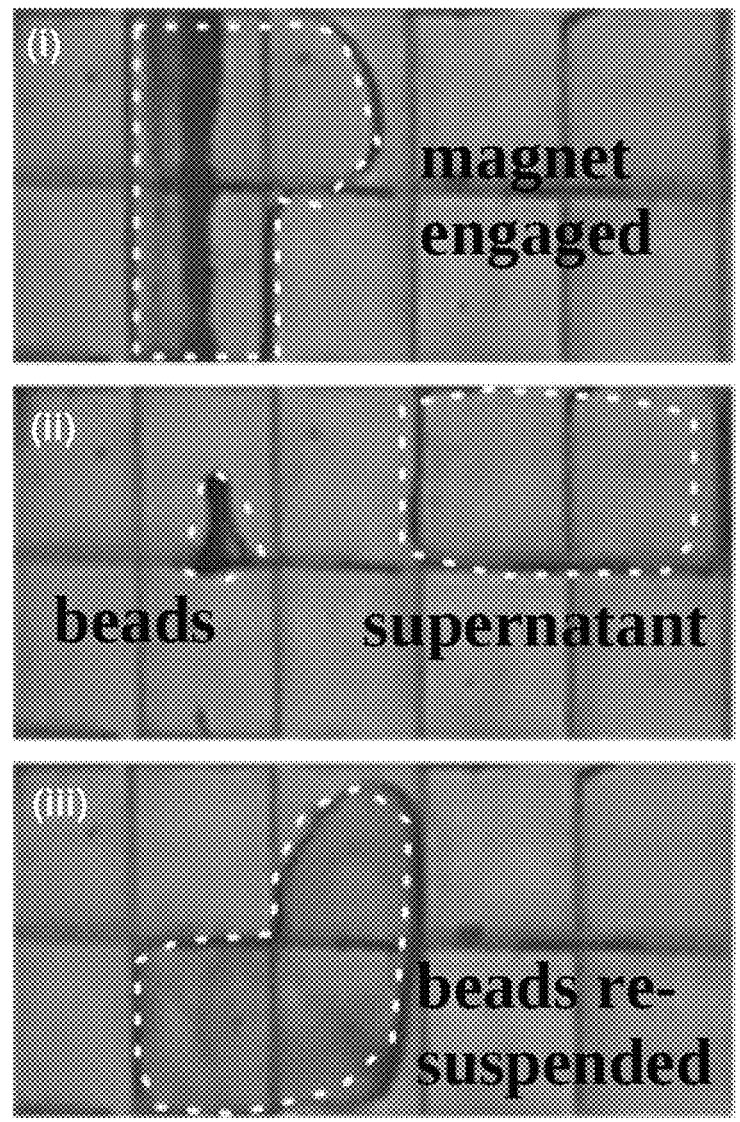
FIG. 16 is a series of still frames from a video sequence showing an example method involving magnetic separation of beads from the supernatant and re-suspension in wash buffer when performing a rubella IgG immunoassay on a paper DMF device with a Luminol/H2O2 chemiluminescent readout.
Figure 17:
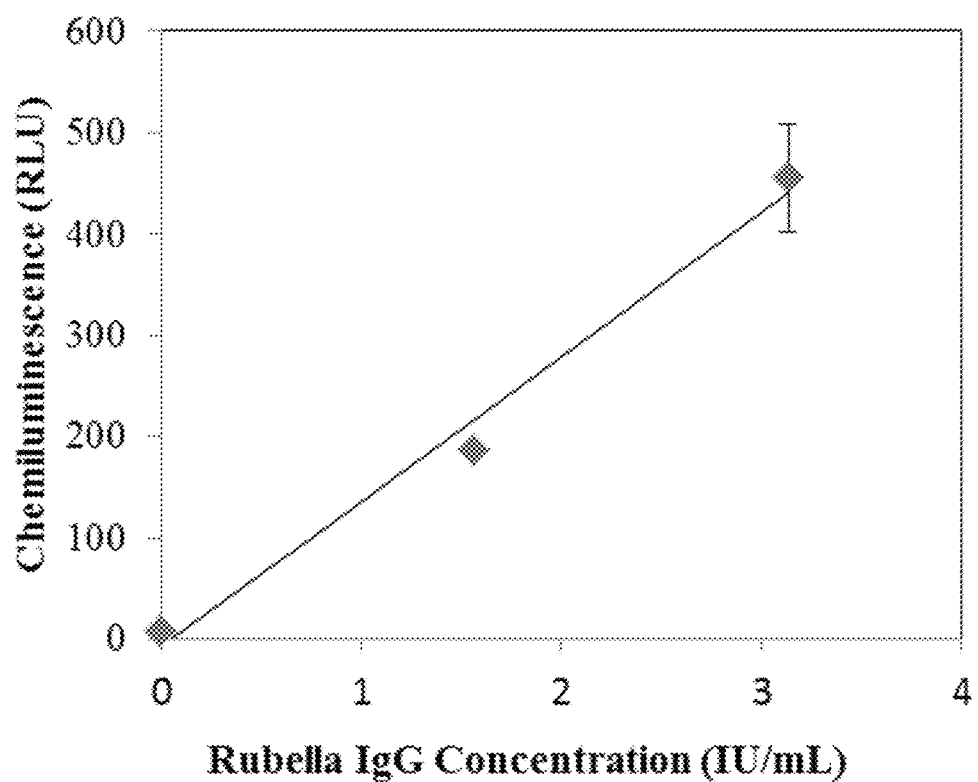
FIG. 17 shows a calibration curve for rubella IgG concentrations of 0, 1.56 and 3.125 IU/mL. Error bars are +/−1 standard deviation.

The ELISA for rubella required a larger electrode array, the use of magnetic-bead-linked antibodies, and a motorized magnet for separation and washing (FIG. 16) [24] 30 discrete steps were required for each concentration evaluated (11 dispense, 10 mix, 8 magnetic separation, and 1 measurement). Most importantly, as shown in FIG. 17, the method was reproducible (R2=0.988) and sensitive (limit of detection=0.15 IU/mL), demonstrating the ability to detect concentrations well below the 10 IU/mL clinical threshold [25]. Since magnetic beads are commercially available for a wide variety of antibodies, it is expected that this procedure can provide a general blueprint toward quantifying a broad range of interesting biomarkers. Moreover, in addition to the obvious benefit of low device cost, this method retains high analytical performance with greatly reduced sample volumes relative to conventional automated immunoassay analyzers [24,26].

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

[1] A. W. Martinez, S. T. Phillips, M. J. Butte, G. M. Whitesides, Angew. Chem. Int. Ed. 2007, 46, 1318-1320.
[2] W. Zhao, A. van den Berg, Lab. Chip 2008, 8, 1988-1991.
[3] X. Li, D. R. Ballerini, W. Shen, Biomicrofluidics 2012, 6, 011301.
[4] G. E. Fridley, H. Q. Le, E. Fu, P. Yager, Lab. Chip 2012, 12, 4321-4327.
[5] A. W. Martinez, S. T. Phillips, E. Carrilho, S. W. Thomas, H. Sindi, G. M. Whitesides, Anal. Chem. 2008, 80, 3699-3707.
[6] C.-M. Cheng, A. W. Martinez, J. Gong, C. R. Mace, S. T. Phillips, E. Carrilho, K. A. Mirica, G. M. Whitesides, Angew. Chem. Int. Ed. 2010, 49, 4771-4774.
[7] A. W. Martinez, S. T. Phillips, G. M. Whitesides, Proc. Natl. Acad. Sci. 2008, 105, 19606-19611.
[8] H. Liu, R. M. Crooks, J. Am. Chem. Soc. 2011, 133, 17564-17566.
[9] E. Fu, B. Lutz, P. Kauffman, P. Yager, Lab. Chip 2010, 10, 918-920.

[10] X. Li, J. Tian, T. Nguyen, W. Shen, Anal. Chem. 2008, 80, 9131-9134.
[11] A. V. Govindarajan, S. Ramachandran, G. D. Vigil, P. Yager, K. F. Böhringer, Lab. Chip 2011, 12, 174-181.
[12] J. Tian, X. Li, W. Shen, Lab. Chip 2011, 11, 2869-2875.
[13] J. Yan, L. Ge, X. Song, M. Yan, S. Ge, J. Yu, Chem.—Eur. J. 2012, 18, 4938-4945.
[14] S. Wang, L. Ge, X. Song, J. Yu, S. Ge, J. Huang, F. Zeng, Biosens. Bioelectron. 2012, 31, 212-218.
[15] S. Wang, L. Ge, X. Song, M. Yan, S. Ge, J. Yu, F. Zeng, Analyst 2012, 137, 3821-3827.
[16] J. Yan, M. Yan, L. Ge, J. Yu, S. Ge, J. Huang, Chem. Commun. 2013, 49, 1383-1385.
[17] K. Choi, A. H. C. Ng, R. Fobel, A. R. Wheeler, Annu. Rev. Anal. Chem. 2012, 5, 413-440.
[18] P. Y. Paik, V. K. Pamula, M. G. Pollack, K. Chakrabarty, in Proc Intl Conf MicroTAS, 2005, pp. 566-568.
[19] J. Gong, C. J. Kim, in Proc. IEEE MEMS, Miami, Fla., 2005, pp. 726-729.
[20] M. Abdelgawad, A. R. Wheeler, Adv. Mater. 2007, 19, 133-137.
[21] M. Abdelgawad, A. Wheeler, Microfluid. Nanofluidics 2008, 4, 349-355.
[22] R. Fobel, C. Fobel, A. R. Wheeler, Appl. Phys. Lett. 2013, 102, 193513.
[23] J. Banatvala, D. Brown, The Lancet 2004, 363, 1127-1137.
[24] K. Choi, A. H. C. Ng, R. Fobel, D. A. Chang-Yen, L. E. Yarnell, E. L. Pearson, C. M. Oleksak, A. T. Fischer, R. P. Luoma, J. M. Robinson, J. Audet, A. R. Wheeler, Anal. Chem. 2013, DOI 10.1021/ac401847x.
[25] L. P. Skendzel, Am. J. Clin. Pathol. 1996, 106, 170-174.
[26] A. H. C. Ng, K. Choi, R. P. Luoma, J. M. Robinson, A. R. Wheeler, Anal. Chem. 2012, 84, 8805-8812.
[27] R. Bollstrom, A. Maattanen, D. Tobjork, P. Ihalainen, N. Kaihovirta, R. Österbacka, J. Peltonen, M. Toivakka, Org. Electron. 2009, 10, 1020-1023.
[28] D. Tobjörk, H. Aarnio, P. Pulkkinen, R. Bollstrom, A. Maattanen, P. Ihalainen, T. Mäkelä, J. Peltonen, M. Toivakka, H. Tenhu, R. Österbacka, Thin Solid Films 2012, 520, 2949-2955.

Therefore what is claimed is:

1. A digital microfluidic device comprising:
a porous substrate having a surface adapted to support electrodes thereon, said porous substrate comprising:
a porous layer formed from a fibrous material; and
a barrier layer provided on said porous layer, wherein said barrier layer is formed from a barrier material suitable for the formation of electrodes thereon;
an array of digital microfluidic electrodes printed on said porous substrate; and
a dielectric layer coating said array of digital microfluidic electrodes, wherein a surface of said dielectric layer is hydrophobic;
wherein a surface roughness of said barrier layer is less than 1 micron, such that said array of digital microfluidic electrodes are suitable for transporting droplets among said digital microfluidic electrodes under electrical actuation, further wherein said barrier layer is a first barrier layer, and said porous layer is a hydrophilic layer, and said porous substrate further comprises a second barrier layer below said hydrophilic layer.

2. The digital microfluidic device according to claim 1 wherein at least an upper portion of said porous substrate is infiltrated.

3. The digital microfluidic device according to claim 1 wherein an inter-electrode trench width is between approximately 5-100 microns.

4. The digital microfluidic device according to claim 1 wherein an inter-electrode trench width is between approximately 5 and 50 microns.

5. The digital microfluidic device according to claim 1 wherein an inter-electrode trench width is between approximately 60 and 90 microns.

6. The digital microfluidic device according to claim 1 wherein an inter-electrode trench depth is less than approximately 1 micron.

7. The digital microfluidic device according to claim 6 wherein said inter-electrode trench depth is less than approximately 500 nm.

8. The digital microfluidic device according to claim 1 wherein the surface roughness of said array of digital microfluidic electrodes is less than approximately 500 nm.

9. The digital microfluidic device according to claim 8 wherein said surface roughness of said array of digital microfluidic electrodes is less than approximately 100 nm.

10. The digital microfluidic device according to claim 1 wherein said fibrous material is a paper-based material.

11. The digital microfluidic device according to claim 10 wherein said fibrous material comprises a cellulosic material.

12. The digital microfluidic device according to claim 1 wherein said fibrous material is a synthetic fibrous material.

13. The digital microfluidic device according to claim 1 wherein said barrier layer comprises kaolin and latex.

14. The digital microfluidic device according to claim 1 wherein said barrier layer is formed directly on said porous layer.

15. The digital microfluidic device according to claim 1 wherein said array of digital microfluidic electrodes is formed directly on said barrier layer.

16. The digital microfluidic device according to claim 1, wherein at least one portion of said first barrier layer removed, thereby exposing a region of said hydrophilic layer.

17. The digital microfluidic device according to claim 16 wherein said region is an electrospray tip formed in said hydrophilic layer.

18. The digital microfluidic device according to claim 16 wherein said region resides below an electrode of said array of digital microfluidic electrodes, and wherein an aperture is formed in said electrode to expose said region.

19. The digital microfluidic device according to claim 18 wherein said hydrophilic layer comprises a microchannel, wherein said microchannel is in fluid communication with a droplet contacting said aperture.

20. The digital microfluidic device according to claim 19 wherein said microchannel is defined by hydrophobic walls formed within said hydrophilic layer.

21. The digital microfluidic device according to claim 18 wherein said hydrophilic layer comprises a lateral flow channel, wherein said lateral flow channel is in fluid communication with a droplet contacting said aperture.

22. The digital microfluidic device according to claim 19 wherein a portion of said microchannel is adjacent to said aperture.

23. The digital microfluidic device according to claim 18 wherein an exposed region of said hydrophilic layer beneath said aperture is surrounded by a hydrophobic wall, thereby forming a hydrophilic pad beneath said aperture.

24. The digital microfluidic device according to claim 23 wherein said hydrophilic pad comprises a dried reagent.

25. The digital microfluidic device according to claim 23 wherein said hydrophilic pad comprises a dried sample.

26. The digital microfluidic device according to claim 1 further comprising a top plate provided in a spaced relationship from said digital microfluidic device, said top plate comprising at least one electrode coated with a dielectric layer, wherein said dielectric layer has a hydrophobic surface.

27. A digital microfluidic device comprising:
a porous substrate having a surface adapted to support electrodes thereon, said porous substrate comprising:
 a porous layer formed from a fibrous material; and
 a barrier layer provided on said porous layer, wherein said barrier layer is formed from a barrier material suitable for the formation of electrodes thereon;
an array of digital microfluidic electrodes formed on said porous substrate; and
a dielectric layer coating said array of digital microfluidic electrodes, wherein a surface of said dielectric layer is hydrophobic;
wherein a surface roughness of said barrier layer is less than 1 micron, such that of said array of digital microfluidic electrodes are suitable for transporting droplets among said digital microfluidic electrodes under electrical actuation
further wherein said barrier layer is a first barrier layer, and said porous layer is a hydrophilic layer, and said porous substrate further comprises a second barrier layer below said hydrophilic layer.

* * * * *